(12) United States Patent
Huber et al.

(10) Patent No.: US 10,077,224 B1
(45) Date of Patent: Sep. 18, 2018

(54) PRODUCTION OF 1,5-PENTANEDIOL VIA UPGRADING OF TETRAHYDROFURFURYL ALCOHOL

(71) Applicant: Wisconsin Alumni Research Foundation, Madison, WI (US)

(72) Inventors: George Willis Huber, Middleton, WI (US); James A. Dumesic, Verona, WI (US); Kevin J. Barnett, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 15/782,593

(22) Filed: Oct. 12, 2017

(51) Int. Cl.
*C07C 31/20* (2006.01)
*C07C 29/04* (2006.01)
*C07C 29/60* (2006.01)

(52) U.S. Cl.
CPC .............. *C07C 31/20* (2013.01); *C07C 29/04* (2013.01); *C07C 29/60* (2013.01)

(58) Field of Classification Search
CPC .......... C07C 29/04; C07C 29/60; C07C 31/20
See application file for complete search history.

(56) References Cited

U.S. PATENT DOCUMENTS 3,702,886 A 11/1972 Argauer et al.

OTHER PUBLICATIONS

Bardin et al. (1998) "Acidity of Keggin-Type Heteropolycompounds Evaluated by Catalytic Probe Reactions, Sorption Microcalorimetry and Density Functional Quantum Chemical Calculations," *J. of Physical Chemistry B*, 102:10817-10825.
Schniepp and Geller (Aug. 1946) "Preparation of Dihydopyran, δ-Hydroxyvaleraldehyde and 1,5-Pentanediol from Tetrahydrofurfuryl Alcohol," *J. Amer. Chem. Soc.* 68(8):1646-1648.

*Primary Examiner* — Sikarl A Witherspoon
(74) *Attorney, Agent, or Firm* — Joseph T. Leone; DeWitt Ross & Stevens S.C.

(57) ABSTRACT

A method of making 1,5-pentanediol from tetrahydrofurfural alcohol. The method includes the steps of dehydrating tetrahydrofurfural alcohol (THFA) to dihydropyran (DHP); hydrating at least a portion of the DHP to 2-hydroxy-tetrahydropyran (2-HY-THP) in the presence of a solid acid catalyst; and hydrogenating at least a portion of the 2-HY-THP to 1,5-pentanediol. The method can be conducted entirely in the absence of noble metal catalysts.

25 Claims, 15 Drawing Sheets

PRODUCTION OF 1,5-PENTANEDIOL VIA UPGRADING OF TETRAHYDROFURFURYL ALCOHOL

FEDERAL FUNDING STATEMENT

This invention was made with government support under DE-EE0006878 awarded by the US Department of Energy. The government has certain rights in the invention.

BACKGROUND

There is currently a growing interest in renewable, chemical production of value-added chemicals from biomass. Among these chemicals are α,ω-diols. These terminal diols are particularly attractive because of the high market prices they command, currently >$2,700/MT (2015 US dollars). 1,5-Pentanediol (1,5-PD) is particularly attractive because it is not currently produced in large quantities from petroleum feedstocks. 1,5-PD is used as a plasticizer and is also used as a precursor in the manufacture of polyurethanes and polyester polyols. In recent academic literature, 1,5-PD is made via direct hydrogenation of furfural and subsequent hydrogenolysis of tetrahydrofurfuryl alcohol:

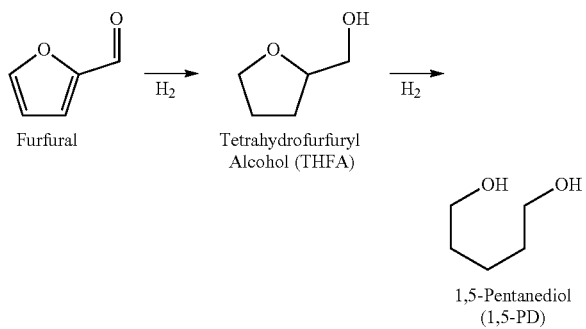

This conventional route has relatively low selectivity and low conversion to 1,5-PD and must run at a relatively high temperature (~250° C. or greater).

Interest in more efficient routes to 1,5-PD is not new. For example, Schniepp and Geller (August 1946) *J. Amer. Chem. Soc.* 68(8):1646-1648, describe a route to 1,5-PD in which tetrahydrofurfural alcohol is converted in the presence of activated alumina to dihydropyran (DHP). The DHP is then hydrated with a homogeneous acid catalyst (0.2 N HCl) to yield a mixture that was approximately 84 wt % gamma-hydroxyvaleraldehyde (i.e., 5-hydroxyvaleraldehyde) and 16 wt % 2-hydroxytetrahydropyran. The reaction mixture is neutralized with base (0.4 N NaOH). Notably, the two intermediates in the mixture were separated via reduced pressure distillation. The last step is performed solely on the 5-hydroxyvaleraldehyde, which is reduced (hydrogenated) to 1,5-PD. The overall yield of 1,5-PD from tetrahydrofurfural alcohol, when the 5-hydroxyvaleraldehyde and 2-hydroxytetrahydropyran were separated prior to the final step, was 70%. However, without the intermediate isolation of the 5-hydroxyvaleraldehyde, the overall yield of 1,5-PD dropped to 60-62%. In both instances, the DHP intermediate was subjected to acid hydrolysis with homogeneous HCl catalysts.

HZSM5-type zeolites (also known as ZSM-5) are known in the literature. See U.S. Pat. No. 3,702,886, issued Nov. 14, 1972 (incorporated herein by reference). This type of zeolite catalyst is widely used in the petroleum industry as a heterogeneous catalyst for hydrocarbon isomerization reactions, for example the isomerization of meta-xylene to para-xylene. HZSM5-type zeolites can be purchased commercially from a large number of suppliers, such as Zeolyst International (Conshohocken, Pa.). HZSM5-type catalysts are aluminosilicate zeolites. Commercial HZSM-5 zeolites (and many others, including H-beta zeolites) are available in a wide range of $SiO_2$-to-$Al_2O_3$ ratios, from approximately 20-to-1 to 300-to-1.

SUMMARY

Disclosed herein is a method to make 1,5-pentanediol (1,5-PD) from biomass in general, and biomass-derived tetrahydrofurfural alcohol (THFA) in particular. The entire pathway from THFA to 1,5-PD is generally referred to herein as the "DHH Route," meaning Dehydration of THFA to dihydropyran (DHP), Hydration of DHP to 2-hydroxytetrahydropyan (2-HY-THP), and Hydrogenation of 2-HY-THP to 1,5-PD:

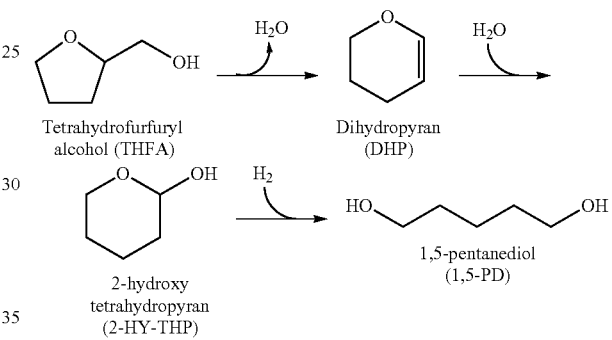

As discussed below, the overall 1,5-PD yield from THFA can be 90% or higher. Additionally, the DHH Pathway does not require the use of noble metal catalysts. Thus, the DHH Pathway is very attractive economically as compared to conventional routes to 1,5-PD. In 2017 dollars, the DHH Pathway yields 1,5-PD at costs below $2,000 per US ton (i.e., short tons).

Disclosed herein is a method to produce 1,5-PD from tetrahydrofurfural alcohol (THFA). In a first step THFA is dehydrated using a metal-oxide catalyst, such as γ-$Al_2O_3$ ($1/kg), to yield dihydropyran (DHP) (See FIG. 11). The DHP is then hydrated in water at low temperatures (e.g., about 20° C. to about 150° C., more preferably about 70° C. to about 100° C.), preferably in the presence of a solid acid catalyst, to yield a product mix containing 2-hydroxytetrahydropyran (2-HY-THP) and 5-hydroxyvaleraldehyde. This product mix is a highly reactive alternative (as compared to THFA) for a subsequent hydrogenation reaction step in which the 2-HY-THP ring-opens to 5-hydroxyvaleraldehyde (5HVal), which hydrogenates to yield 1,5-PD. This can be accomplished using a number of different metallic catalysts. Preferred both on cost and performance grounds are Ru/$TiO_2$, Ru/Carbon, and Pt/ZSM5 catalysts. The conversion of 2-HY-THP occurs at rates that are about 100-fold faster than the corresponding reaction with THFA. The conversion of 2-HY-THP can be catalyzed using relatively inexpensive base metal catalysts (rather than very expensive noble metal catalysts).

The method can also be carried out at relatively mild reaction conditions, without the need of added homogenous acid (and thus without the need to neutralize any acid). The method also incurs far lower separation costs. The method results in >90% overall yields to 1,5-PD (based on THFA).

Disclosed herein is a method of making 1,5-pentanediol. The method comprises dehydrating tetrahydrofurfural alcohol (THFA) to dihydropyran (DHP), hydrating at least a portion of the DHP to a product mix containing 2-hydroxy-tetrahydropyran (2-HY-THP) and 5-hydroxyvaleraldehyde in the presence of a solid acid catalyst, and hydrogenating at least a portion of the 2-HY-THP:5HVal mixture to 1,5-pentanediol.

The solid acid catalyst for the hydration step may be a solid Brønsted acid catalyst, a solid Lewis acid catalyst, and/or combinations thereof. Suitable solid acid catalysts include, but are not limited to, zeolites, metal oxides, sulfonic acid-modified polymers (for example, Nafion-brand or Amberlyst-brand resins), salts of phosphotungstic acid (for example, cesium phosphotungstate, CsPTA), zirconium phosphate, and the like. Aluminosilicate zeolites are generally preferred, with the zeolites HZSM5 and H-Beta being most preferred.

The THFA can be dehydrated by contacting it with a solid acid catalyst, such as a solid Brønsted acid catalyst, a solid Lewis acid catalyst, and combinations thereof. The dehydration step may be conducted on neat THFA or on an aqueous solution of THFA in which the THFA is present in the aqueous solution in a concentration of from about 5 wt % to about 99 wt %. Preferably, the dehydration step occurs at a temperature of from about 200° C. to about 500° C. (more preferably 275° C. to about 450° C.) and a pressure of from about 1 atm to about 5 atm.

The hydration step (DHP to 2-HY-THP) occurs in the presence of water and in the presence of a solid acid catalyst. Preferably the hydration step occurs and at a temperature of from about 20° C. to about 200° C., more preferably 20° C. to about 150° C. The DHP is preferably present with the water in a concentration of from about 5 wt % to about 80 wt %.

The hydrogenation reaction of the 2-HY-THP:5HVal mixture to 1,5-PD is preferably accomplished by contacting the 2-HY-THP:5HVal mixture with a catalyst comprising a metal selected from the group consisting of Ti, V, Fe, Co, Ni, Cu, Mo, Ru, Rh, Pd, Ag, Re, Ir, Pt, Au and combinations thereof, for a time and at a temperature sufficient to yield 1,5-PD. Many of these catalysts result in essentially quantitative yield of 1,5-PD from 2-HY-THP. Preferred catalysts are Ru, NiMo, NiRe, NiV, NiTi, Ni, Fe, Co, Rh, RhRe, RhMo, Pt and PtMo. The selected catalyst(s) may be optionally deposited on a support, such as a carbon or metal-oxide support.

Thus, a more specific version of the method comprises dehydrating tetrahydrofurfural alcohol (THFA) to dihydropyran (DHP) by contacting the THFA with a solid acid catalyst at a temperature of from about 200° C. to about 500° C., and a pressure of from about 1 atm to about 5 atm; hydrating at least a portion of the DHP to 2-hydroxy-tetrahydropyran (2-HY-THP) in the absence of homogeneous acid at a temperature of from about 20° C. to about 200° C.; and hydrogenating at least a portion of the 2-HY-THP:5HVal mixture to 1,5-pentanediol by contacting the 2-HY-THP:5HVal mixture with a catalyst comprising a metal selected from the group consisting of Ti, V, Fe, Co, Ni, Cu, Mo, Ru, Rh, Pd, Ag, Re, Ir, Pt, Au and combinations thereof. The various catalyst and supports noted previously may be used.

Squares=1,5-PD. Circles=THP-oxypentanol. Triangles=THP-oxypentanal. Diamonds=2,2'-HY-THP.

Figure 15:
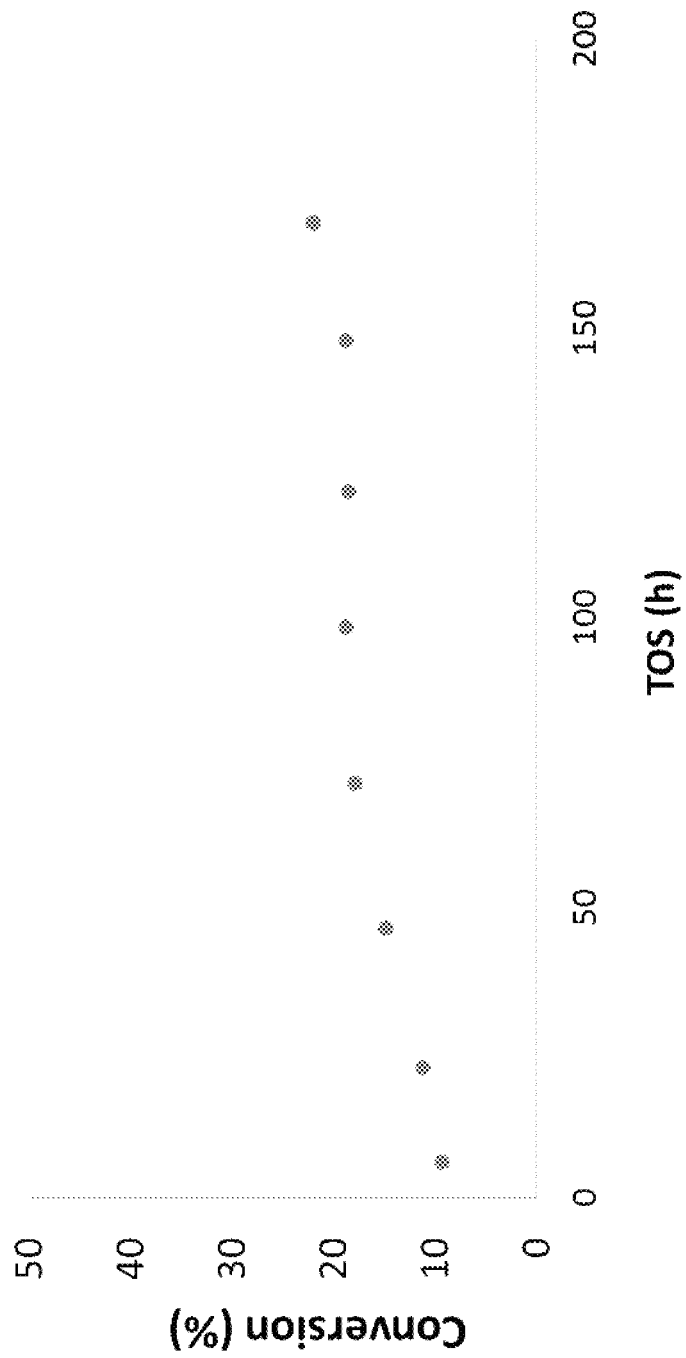

FIG. 15 is a graph depicting conversion of 2-HY-THP to 1,5-pentanediol (y-axis) over a 0.59% Pt/HZSM5 catalyst in a continuous flow reactor for several hours time-on-stream (x-axis).

DETAILED DESCRIPTION

Abbreviations and Definitions

"Biomass" as used herein includes materials containing cellulose, hemicellulose, lignin, protein and carbohydrates such as starch and sugar. Common forms of biomass include trees, shrubs and grasses, corn and corn husks as well as municipal solid waste, waste paper and yard waste. Biomass high in starch, sugar or protein such as corn, grains, fruits and vegetables, is usually consumed as food. Conversely, biomass high in cellulose, hemicellulose and lignin is not readily digestible by humans and is primarily utilized for wood and paper products, fuel, or is discarded as waste. "Biomass" as used herein explicitly includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, vines, hard and soft woods. In addition, biomass includes organic waste materials generated from agricultural processes including farming and forestry activities, specifically including forestry wood waste. "Biomass" includes virgin biomass and/or non-virgin biomass such as agricultural biomass, commercial organics, construction and demolition debris, municipal solid waste, waste paper, and yard waste. Municipal solid waste generally includes garbage, trash, rubbish, refuse and offal that is normally disposed of by the occupants of residential dwelling units and by business, industrial and commercial establishments, including but not limited to: paper and cardboard, plastics, food scraps, scrap wood, saw dust, and the like.

"Biomass-derived"=Compounds or compositions fabricated or purified from biomass. Glucose and HMF for use in the disclosed method may be biomass-derived.

Brønsted-Lowry Acid/Base=A Brønsted-Lowry acid is defined herein as any chemical species (atom, ion, molecule, compound, complex, etc.), without limitation, that can donate or transfer one or more protons to another chemical species. Mono-protic, diprotic, and triprotic acids are explicitly included within the definition. A Brønsted-Lowry base is defined herein as any chemical species that can accept a proton from another chemical species. Included among Brønsted-Lowry acids are mineral acids, organic acids, heteropolyacids, solid acid catalysts, zeolites, etc. as defined herein. Note that this list is exemplary, not exclusive. The shortened term "Brønsted" is also used synonymously with "Brønsted-Lowry."

"Carbohydrate" is defined herein as a compound that consists only of carbon, hydrogen, and oxygen atoms, in any ratio.

"$C_5$ carbohydrate" refers to any carbohydrate, without limitation, that has five (5) carbon atoms. The definition includes pentose sugars of any description and stereoisomerism (e.g., D/L aldopentoses and D/L ketopentoses). $C_5$ carbohydrates include (by way of example and not limitation) arabinose, lyxose, ribose, ribulose, xylose, and xylulose.

"$C_6$ carbohydrate" refers to any carbohydrate, without limitation, that has six (6) carbon atoms. The definition includes hexose sugars of any description and stereoisomerism (e.g., D/L aldohexoses and D/L ketohexoses). $C_6$ carbohydrates include (by way of example and not limitation) allose, altrose, fructose, galactose, glucose, gulose, idose, mannose, psicose, sorbose, tagatose, and talose.

"Cellulose" refers to a polysaccharide of glucose monomers ($(C_6H_{10}O_5)_n$); "cellulosic biomass" refers to biomass as described earlier that comprises cellulose, and/or consists essentially of cellulose, and/or consists entirely of cellulose. Lignocellulosic biomass refers to biomass comprising cellulose, hemicellulose, and lignin. Lignocellulosic biomass comprises xylose, as does hemicellulose.

"Dehydration catalyst" means any catalyst, without limitation, whether now known or developed in the future, capable of removing water from organic compounds.

"Glucose-containing oligomers, glucose-containing polymers, Glucose-containing reactant, C6-containing reactant"=Any chemical species, having any type of intramolecular bond type, that comprises a glucose unit. The definition explicitly includes glucose-containing disaccharides (such as, but not limited to, sucrose, lactose, maltose, trehalose, cellobiose, kojibiose, nigerose, isomaltose, β,β-trehalose, α,β-trehalose, sophorose, laminaribiose, gentiobiose, turanose, maltulose, palatinose, gentiobiulose, etc.), trisaccharides (such as, but not limited to, isomaltotriose, nigerotriose, maltotriose, maltotriulose, raffinose, etc.), and larger oligosaccharides and polysaccharides, as well as large and more complex glucose-containing polymers and carbohydrates, such as, but not limited to, starch, amylase, amylopectin, glycogen, cellulose, hemicelluloses (e.g., xyloglucan, glucomannan, etc.), lignocellulose, and the like. Linear, branched, and macrocyclic oligomers and polymers containing glucose are explicitly included within the definition.

"Heteropolyacid"=A class of solid-phase acids exemplified by such species as $H_4SiW_{12}O_{40}$, $H_3PW_{12}O_{40}$, $H_6P_2W_{18}O_{62}$, $H_{3+x}PMo_{12-x}V_xO_{40}$ and the like. Heteropolyacids are solid-phase acids having a well-defined local structure, the most common of which is the tungsten-based Keggin structure. The Keggin unit comprises a central $PO_4$ tetrahedron, surrounded by 12 $WO_6$ octahedra. The standard unit has a net (⁻3) charge, and thus requires three cations to satisfy electroneutrality. If the cations are protons, the material functions as a Brønsted acid. The acidity of these compounds (as well as other physical characteristics) can be "tuned" by substituting different metals in place of tungsten in the Keggin structure. See, for example, Bardin et al. (1998) "Acidity of Keggin-Type Heteropolycompounds Evaluated by Catalytic Probe Reactions, Sorption Microcalorimetry and Density Functional Quantum Chemical Calculations," *J. of Physical Chemistry B*, 102:10817-10825.

"Homogeneous catalyst"=A catalyst that exists in the same phase (solid, liquid, or gas) as the reactants under reaction conditions. "Heterogeneous catalyst"=A catalyst that exists in a different phase than the reactants under reaction conditions.

"Hydrofuran" is used herein to refer to any unsubstituted or substituted cyclic ether having a single oxygen heteroatom in the ring, and having five total atoms in the ring and which is derived from furanic compounds. Hydrofurans that are miscible in water, such as tetrahydrofuran (THF), are more appropriate for use in the monophasic reactions described herein. In the biphasic reactions, any hydrofuran may be used.

"Hydropyran" is used herein to refer to any unsubstituted or substituted cyclic ether having a single oxygen heteroatom in the ring, and having six total atoms in the ring and which is derived from pyranic compounds. Hydropyrans miscible in water are more appropriate for use in the monophasic reactions described herein. In the biphasic reactions, any hydropyran may be used.

1,5-PD=1,5-pentanediol. 2-HY-THP=2-hydroxy-tetrahydropyran. 5-HVal=5-hydroxyvaleraldehyde. DHP=dihydropyran. HMF=5-hydroxymethylfurfural. SMSI=strong metal-support interaction. THFA=tetrahydrofurfuryl alcohol. Mineral acid=any mineral-containing acid, including (by way of example and not limitation), hydrochloric acid, nitric acid, phosphoric acid, SA, boric acid, hydrofluoric acid, hydrobromic acid, and the like. WHSV=reactant weight hourly space velocity.

Lewis Acid/Base=A Lewis acid is defined herein as any chemical species that is an electron-pair acceptor, i.e., any chemical species that is capable of receiving an electron pair, without limitation. A Lewis base is defined herein as any chemical species that is an electron-pair donor, that is, any chemical species that is capable of donating an electron pair, without limitation.

The Lewis acid (also referred to as the Lewis acid catalyst) may be any Lewis acid based on transition metals, lathanoid metals, and metals from Group 4, 5, 13, 14 and 15 of the periodic table of the elements, including boron, aluminum, gallium, indium, titanium, zirconium, tin, vanadium, arsenic, antimony, bismuth, lanthanum, dysprosium, and ytterbium. One skilled in the art will recognize that some elements are better suited in the practice of the method. Illustrative examples include $AlCl_3$, $(alkyl)AlCl_2$, $(C_2H_5)_2AlCl$, $(C_2H_5)_3Al_2Cl_3$, $BF_3$, $SnCl_4$ and $TiCl_4$.

The Group 4, 5 and 14 Lewis acids generally are designated by the formula $MX_4$; wherein M is Group 4, 5, or 14 metal, and X is a halogen independently selected from the group consisting of fluorine, chlorine, bromine, and iodine, preferably chlorine. X may also be a psuedohalogen. Non-limiting examples include titanium tetrachloride, titanium tetrabromide, vanadium tetrachloride, tin tetrachloride and zirconium tetrachloride. The Group 4, 5, or 14 Lewis acids may also contain more than one type of halogen. Non-limiting examples include titanium bromide trichloride, titanium dibromide dichloride, vanadium bromide trichloride, and tin chloride trifluoride.

Group 4, 5 and 14 Lewis acids useful in the method may also have the general formula $MR_nX_{4-n}$; wherein M is Group 4, 5, or 14 metal; wherein R is a monovalent hydrocarbon radical selected from the group consisting of $C_1$ to $C_{12}$ alkyl, aryl, arylalkyl, alkylaryl and cycloalkyl radicals; wherein n is an integer from 0 to 4; and wherein X is a halogen independently selected from the group consisting of fluorine, chlorine, bromine, and iodine, preferably chlorine. X may also be a psuedohalogen. Non-limiting examples include benzyltitanium trichloride, dibenzyltitanium dichloride, benzylzirconium trichloride, dibenzylzirconium dibromide, methyltitanium trichloride, dimethyltitanium difluoride, dimethyltin dichloride and phenylvanadium trichloride.

Group 4, 5 and 14 Lewis acids useful in method may also have the general formula $M(RO)_nR'_mX_{(m+n)}$; wherein M is Group 4, 5, or 14 metal; RO is a monovalent hydrocarboxy radical selected from the group consisting of $C_1$ to $C_{30}$ alkoxy, aryloxy, arylalkoxy, alkylaryloxy radicals; R' is a monovalent hydrocarbon radical selected from the group consisting of $C_1$ to $C_{12}$ alkyl, aryl, arylalkyl, alkylaryl and cycloalkyl radicals; n is an integer from 0 to 4; m is an integer from 0 to 4 such that the sum of n and m is not more than 4; and X is a halogen independently selected from the group consisting of fluorine, chlorine, bromine, and iodine, preferably chlorine. X may also be a psuedohalogen. Non-limiting examples include methoxytitanium trichloride, n-butoxytitanium trichloride, di(isopropoxy)titanium dichloride, phenoxytitanium tribromide, phenylmethoxyzirconium trifluoride, methyl methoxytitanium dichloride, methyl methoxytin dichloride and benzyl isopropoxyvanadium dichloride.

Group 5 Lewis acids may also have the general formula $MOX_3$; wherein M is a Group 5 metal; X is a halogen independently selected from the group consisting of fluorine, chlorine, bromine, and iodine, preferably chlorine. A non-limiting example is vanadium oxytrichloride.

The Group 13 Lewis acids have the general formula $MX_3$; wherein M is a Group 13 metal and X is a halogen independently selected from the group consisting of fluorine, chlorine, bromine, and iodine, preferably chlorine. X may also be a psuedohalogen. Non-limiting examples include aluminum trichloride, boron trifluoride, gallium trichloride, indium trifluoride, and the like.

The Group 13 Lewis acids useful in method may also have the general formula: $MR_nX_{3-n}$ wherein M is a Group 13 metal; R is a monovalent hydrocarbon radical selected from the group consisting of $C_1$ to $C_{12}$ alkyl, aryl, arylalkyl, alkylaryl and cycloalkyl radicals; and n is an number from 0 to 3; and X is a halogen independently selected from the group consisting of fluorine, chlorine, bromine, and iodine, preferably chlorine. X may also be a psuedohalogen. Non-limiting examples include ethylaluminum dichloride, methylaluminum dichloride, benzylaluminum dichloride, isobutylgallium dichloride, diethylaluminum chloride, dimethylaluminum chloride, ethylaluminum sesquichloride, methylaluminum sesquichloride, trimethylaluminum and triethylaluminum.

Group 13 Lewis acids useful in this disclosure may also have the general formula $M(RO)_nR'_mX_{3-(m+n)}$; wherein M is a Group 13 metal; RO is a monovalent hydrocarboxy radical selected from the group consisting of $C_1$ to $C_{30}$ alkoxy, aryloxy, arylalkoxy, alkylaryloxy radicals; R' is a monovalent hydrocarbon radical selected from the group consisting of $C_1$ to $C_{12}$ alkyl, aryl, arylalkyl, alkylaryl and cycloalkyl radicals; n is a number from 0 to 3; m is an number from 0 to 3 such that the sum of n and m is not more than 3; and X is a halogen independently selected from the group consisting of fluorine, chlorine, bromine, and iodine, preferably chlorine. X may also be a psuedohalogen. Non-limiting examples include methoxyaluminum dichloride, ethoxyaluminum dichloride, 2,6-di-tert-butylphenoxyaluminum dichloride, methoxy methylaluminum chloride, 2,6-di-tert-butylphenoxy methylaluminum chloride, isopropoxygallium dichloride and phenoxy methylindium fluoride.

Group 13 Lewis acids useful in this disclosure may also have the general formula $M(RC(O)O)_nR'_mX_{3-(m+n)}$; wherein M is a Group 13 metal; RC(O)O is a monovalent hydrocarbacyl radical selected from the group consisting of $C_2$ to $C_{30}$ alkacyloxy, arylacyloxy, arylalkylacyloxy, alkylarylacyloxy radicals; R' is a monovalent hydrocarbon radical selected from the group consisting of $C_1$ to $C_{12}$ alkyl, aryl, arylalkyl, alkylaryl and cycloalkyl radicals; n is a number from 0 to 3 and m is a number from 0 to 3 such that the sum of n and m is not more than 3; and X is a halogen independently selected from the group consisting of fluorine, chlorine, bromine, and iodine, preferably chlorine. X may also be a psuedohalogen. Non-limiting examples include acetoxyaluminum dichloride, benzoyloxyaluminum dibromide, benzoyloxygallium difluoride, methyl acetoxyaluminum chloride, and isopropoyloxyindium trichloride.

The most preferred Lewis acids for use in the method are metal halides generally and more specifically transition metal halides, lathanoid metal halides, and Group 5, 13, and 14 metal halides. Preferred among the metal halides are metal chlorides. Preferred transition metal chlorides include, but are not limited to, $TiCl_4$, $VCl_3$. and the like. Preferred Group 13 and 14 metal halides and chlorides include, but are not limited to, $BF_3$, $AlCl_3$, $SnCl_4$, $InCl_3$, and $GaCl_3$. Preferred lanthanoid chlorides include, but are not limited to, $LaCl_3$, $DyCl_3$ and $YbCl_3$.

"Noble metal" is used herein to include ruthenium, rhodium, palladium, silver, osmium, iridium, platinum, gold, and rhenium. Other corrosion-resistant metals that can be used as catalysts in the subject process include titanium, niobium, and tantalum.

The terms "solid acid" and "solid acid catalyst" are used synonymously herein and can comprise one or more solid acid materials. The solid acid catalyst can be used independently or alternatively can be utilized in combination with one or more mineral acid or other types of catalysts. Exemplary solid acid catalysts which can be utilized include, but are not limited to, heteropolyacids, acid resin-type catalysts, mesoporous silicas, acid clays, sulfated zirconia, molecular sieve materials, zeolites, and acidic material on a thermo-stable support. Where an acidic material is provided on a thermo-stable support, the thermo-stable support can include for example, one or more of carbon, alpha-alumina, and the like. The oxides themselves (e.g., $ZrO_2$, $SnO_2$, $TiO_2$, etc.) which may optionally be doped with additional acid groups such as $SO_4^{2-}$ or $SO_3H$ may also be used as solid acid catalysts.

Further examples of solid acid catalysts include strongly acidic ion exchangers such as cross-linked polystyrene containing sulfonic acid groups. For example, the Amberlyst®-brand resins are functionalized styrene-divinylbenzene copolymers with different surface properties and porosities. (These types of resins are designated herein as "Amb" resins, followed by a numeric identifier of the specific sub-type of resin where appropriate.) The functional group is generally of the sulfonic acid type. The Amberlyst®-brand resins are supplied as gellular or macro-reticular spherical beads. (Amberlyst® is a registered trademark of the Dow Chemical Co.) Similarly, Nafion®-brand resins are sulfonated tetrafluoroethylene-based fluoropolymer-copolymers which are solid acid catalysts. Nafion® is a registered trademark of E.I. du Pont de Nemours & Co.)

Solid catalysts can be in any shape or form now known or developed in the future, such as, but not limited to, granules, powder, beads, pills, pellets, flakes, cylinders, spheres, or other shapes.

Supports for metal catalysts can be any suitable support (now known or developed in the future) that is sufficiently robust to withstand the reaction conditions disclosed herein. Suitable catalyst supports include, by way of example and not limitation, alumina, carbon, ceria, magnesia, niobia, silica, titania, zirconia, zeolites (preferably, Y, ZSM 5, MWW and beta), hydrotalcite, molecular sieves, clays, iron oxide, silicon carbide, aluminosilicates, and modifications, mixtures or combinations thereof.

WHSV=weight hourly space velocity.

Zeolites may also be used as solid acid catalysts. Of these, H-type zeolites are generally preferred, for example zeolites in the mordenite group or fine-pored zeolites such as zeolites X, Y and L, e.g., mordenite, erionite, chabazite, or faujasite. Also suitable are ultrastable zeolites in the faujasite group which have been dealuminated.

TOF=Turnover frequency. TOS=Time on stream.

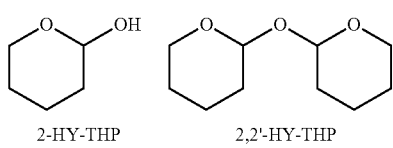

2-HY-THP  2,2'-HY-THP

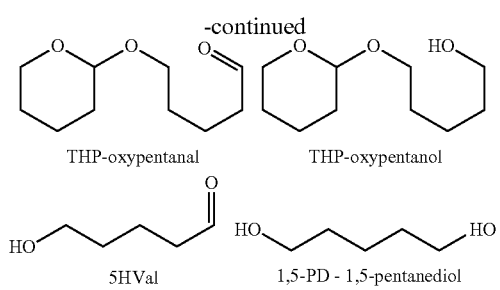

THP-oxypentanal   THP-oxypentanol

5HVal   1,5-PD - 1,5-pentanediol

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, 5, 6, from 1 to 9, from 3.6 to 4.6, from 3.5 to 9.9, and so forth.

All references to singular characteristics or limitations shall include the corresponding plural characteristic or limitation, and vice-versa, unless otherwise specified or clearly implied to the contrary by the context in which the reference is made.

The processes described herein can be run in batch mode, semi-continuous mode, and/or continuous mode, all of which are explicitly included herein.

All combinations of method or process steps as used herein can be performed in any order, unless otherwise specified or clearly implied to the contrary by the context in which the referenced combination is made.

The methods described and claimed herein can comprise, consist of, or consist essentially of the essential elements and limitations of the disclosed methods, as well as any additional or optional ingredients, components, or limitations described herein or otherwise useful in synthetic organic chemistry.

The Method:

The method proceeds in three steps:

(1) dehydrating tetrahydrofurfural alcohol (THFA) to dihydropyran (DHP);

(2) hydrating at least a portion of the DHP to 2-hydroxy-tetrahydropyran (2-HY-THP) in the presence of a solid acid catalyst; and (3) hydrogenating at least a portion of the 2-HY-THP to 1,5-pentanediol, preferably in the presence of a metal-containing catalyst.

Step 1, the THFA dehydration, preferably occurs over a solid acid catalyst as defined above. Preferred is a γ-$Al_2O_3$ catalyst, which afforded >93% yield to DHP. (See FIG. 11, discussed below.)

Step 2, the DHP hydration, does not require any catalyst, but has a vastly increased rate in the presence of a solid acid catalyst (which is preferred). It takes place in water and afforded approximately 94% yield to 2-HY-THP Step 3, the 2-HY-THP hydrogenolysis was substantially quantitative when NiMo/carbon was used as the catalyst; the reaction afforded ~100% yield to 1,5-PD.

The overall three-step process (from THFA) is depicted below:

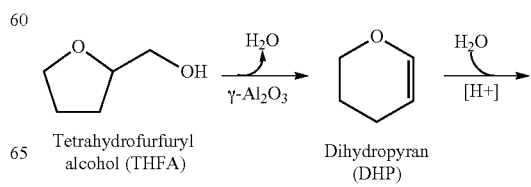

Tetrahydrofurfuryl alcohol (THFA)   Dihydropyran (DHP)

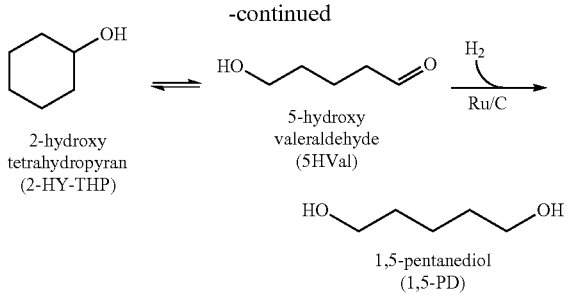

2-hydroxy tetrahydropyran (2-HY-THP) ⇌ 5-hydroxy valeraldehyde (5HVal) →(H₂, Ru/C) 1,5-pentanediol (1,5-PD)

A huge benefit of the method is its overall costs, which is vastly cheaper than conventional routes that require using noble metal catalyst. Table 1 is a brief comparison of the cost of the catalysts typically used in the conventional dehydration route to 1,5-PD, versus the cost of the catalysts used in the current method.

TABLE 1

Comparative Cost of Catalysts

| Catalysts used in conventional route to 1,5-PD | Price ($/kg, 2014) | Preferred catalysts used in present method | Price ($/kg, 2014) |
|---|---|---|---|
| Rh | $38,000 | γ-Al₂O₃ | <$1 |
| Ir | $18,000 | NiMo/Carbon | Ni: $17 |
| Pt | $46,000 | | Mo: $27 |
| Re | $3,000 | Co/TiO₂ | Co: $31 |
| | | | TiO₂: <$1 |

As shown in Table 1, the present method yield 1,5-PD at a catalyst cost that is roughly 10,000-fold less than the catalyst cost of the conventional route. We have estimated that production costs (in 2014 dollars) for producing 1,5-PD by hydrogenolysis of THFA using a noble metal catalyst is approximately $582/ton 1,5-PD. This corresponds to an economic potential of −$281/ton 1,5-PD for this route.

In contrast, the present method need not utilize noble metal catalysts. The present method, however, may utilize noble metal catalysts. It also operates at higher reactant concentrations, so energy costs relating to product distillation are slashed as well. In contrast to the hydrogenolysis of THFA route, 1,5-PD can be produced via the present method for an estimated cost of approximately $77/ton. This corresponds to an economic potential of +$439/ton 1,5-PD. In short, the present route represents an immense upgrade from the THFA hydrogenolysis route economically.

Moreover, the present method, despite its greatly reduced costs, results in improved yields. For example, Table 2 compares the requirements and yields of the present method versus the route described by Schniepp and Geller (August 1946) *J. Amer. Chem. Soc.* 68(8):1646-1648.

TABLE 2

Requirements and yields as compared to Schniepp and Geller (1946)

| | Criteria | Schniepp and Geller (1946) | Huber/Dumesic (2015) |
|---|---|---|---|
| Step 1: THFA Dehydration | Feed Catalyst Yield | 100% THFA vapor γ-Al₂O₃ 89% | 100% THFA vapor γ-Al₂O₃ >93% |
| Step 2: DHP Hydration | Feed Catalyst Yield | 20% DHP/H₂O 0.2N HCl 78% 5-hydroxy-valeraldehyde | 50% DHP/H₂O Solid Acid or No Catalyst 94% 2-HY-THP |
| Step 3: 1,5-PD Formation | Feed Catalyst Yield | 5-hydroxy-valeraldehyde Copper-chromite ~100% | 2-HY-THP Ru/C or Pt/ZSM5 ~100% |
| Step Integration | Step 2 + Step 3 Yield | 61% | 94% |
| | Overall Yield (sum of separate steps) | 70% | >90% |

In short, as compared to the Schniepp and Geller approach, overall yield in the present method increased from ~70% to >90%. Additionally, in the present method there is no need for a mineral acid catalyst (HCl) in DHP hydration step. Omitting the need for a mineral acid catalyst also does away with the additional step of neutralizing the acid prior to the next step in the method. This eliminates a difficult and costly separation/neutralization of homogeneous acid.

A number of catalysts give 100% yields to 1,5-PD from 2-HY-THP. Among these catalysts are NiMo, NiRe, NiV, NiTi, Ni, Fe, Co, Rh, RhRe, RhMo, Pt, and PtMo.

Table 3 shows the results for continuous flow reactions after 12 hours time on stream when using various solid acid catalysts for the first step, dehydration of THFA to DHP:

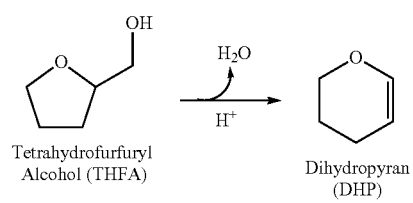

Tetrahydrofurfuryl Alcohol (THFA) →(H₂O, H⁺) Dihydropyran (DHP)

TABLE 3

Vapor-Phase THFA Dehydration: Acid Catalysts

| Catalyst | Mass of Catalyst (mg) | Rxn Temp (° C.) | Pressure (atm) | Reactant (wt %) | Solvent (wt %) | Conversion (%) | Selectivity to DHP (%) | Selectivity to Unknown Products (%) |
|---|---|---|---|---|---|---|---|---|
| γ-Al₂O₃ | 150 | 375 | 1 | THFA - 100% | N/A | 100 | 93 | 0.5 |
| Silica Alumina | 25 | 350 | 1 | THFA - 20% | MeOH - 80% | 95 | 46 | 10 |

TABLE 3-continued

Vapor-Phase THFA Dehydration: Acid Catalysts

| Catalyst | Mass of Catalyst (mg) | Rxn Temp (° C.) | Pressure (atm) | Reactant (wt %) | Solvent (wt %) | Conversion (%) | Selectivity to DHP (%) | Selectivity to Unknown Products (%) |
|---|---|---|---|---|---|---|---|---|
| ZrO$_2$ | 130 | 375 | 1 | THFA - 100% | N/A | 40 | 80 | 6 |

Table 4 depicts the results of the hydration reaction, DHP to 2-HY-THP:

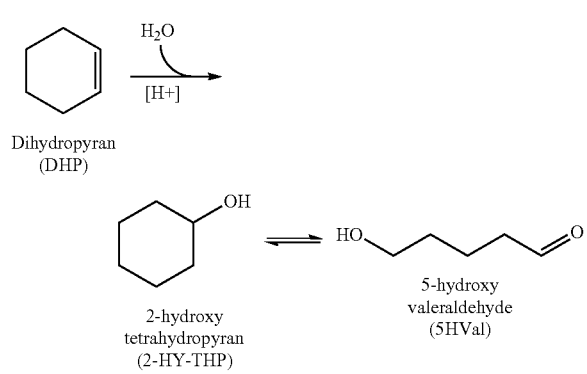

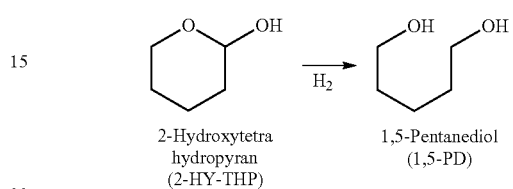

TABLE 4

DHP to 2-HY-THP

| Catalyst | Reaction Temp (° C.) | Reaction Time (hr) | Reactant (wt %) | Solvent (wt %) | Conversion (%) | Selectivity to 2-HY-THP (%) |
|---|---|---|---|---|---|---|
| N/A | 70 | 12 | DHP-50% | H$_2$O-50% | 100 | 94 |

As shown in Table 4, the DHP can be converted into 2-HY-THP in very high yields (94%). This step represents a departure from the Schniepp and Geller (1946) approach, which seeks to maximize the production of 5-hydroxyvaleraldehyde (78%; see Table 2), rather than 2-HY-THP as in the present method (94%; see Table 4). Schniepp and Geller fail to recognize that the 2-HY-THP can be maximized more than the yield to 5-hydroxyvaleraldehyde. Because the final hydrogenation step is substantially quantitative, the overall yield of the present method is much improved as compared to the Schniepp and Geller route. In the present approach, the two typically are not separated (although that is an option). Separation by distillation or any other means simply is not required because purification of the intermediate is not necessary to quantitatively produce 1,5-PD, in contrast to the Schniepp and Geller route.

As shown in Tables 5A and 5B, the final step, 2-HY-THP to 1,5-PD, is substantially quantitative using a number of different base metal and noble metal catalysts:

TABLE 5A

2-HY-THP Results: Catalyst Screening

| Catalyst | Mass Catalyst (g) | Reaction Time (min) | Conversion (%) | Rate of Formation of 1,5-PD (µmol/(min*gcat)) | Selectivity to 1,5-PD (%) |
|---|---|---|---|---|---|
| 1:1 NiMo/C | 0.001 | 60 | 22.5 | 8916 | 100.0% |
| 1:0.5 NiMo/SiO$_2$ | 0.001 | 60 | 15.8 | 6359 | 100.0% |
| 1:0.2 NiRe/C | 0.001 | 60 | 16 | 5505 | 100.0% |
| 1:0.25 NiMo/C | 0.001 | 60 | 8.7 | 4075 | 100.0% |
| 1:0.25 NiW/SiO$_2$ | 0.001 | 60 | 11.2 | 4014 | 100.0% |
| 1:0.1 NiMo/C | 0.001 | 60 | 6.4 | 2465 | 100.0% |
| 1:0.1 NiV/SiO$_2$ | 0.001 | 60 | 7.4 | 2305 | 94.5% |
| 1:0.5 NiNb/SiO$_2$ | 0.001 | 60 | 4.9 | 1213 | 77.2% |
| 1:0.5 NiTi/SiO$_2$ | 0.001 | 60 | 3.7 | 2057 | 100.0% |
| Pt/C | 0.0056 | 180 | 30.7 | 748 | 100.0% |
| Ni/SiO$_2$ | 0.0098 | 60 | 6.3 | 574 | 100.0% |
| Rh/C | 0.0055 | 180 | 21.8 | 508 | 100.0% |
| Co/SiO2 | 0.0257 | 240 | 10.5 | 37 | 99.7% |
| FePK/Al$_2$O$_3$ | 0.0263 | 180 | 4.5 | 31 | 100.0% |
| 1:0.1 RhMo/C | 0.005 | 60 | 99* | 7700 | 100.0% |
| 1:1RhRe/C | 0.005 | 60 | 99* | 7700 | 100.0% |
| BASF Cu | 0.0251 | 360 | 75* | 153 | 88.0% |

TABLE 5B

2-HY-THP Results: Catalyst Screening (More)

| Catalyst | Rate per gram Metal (µmol/(min*g metal)) | Rate per Total Parent Metal Sites (1/s) | Rate per Parent Metal Surface Sites (1/s) |
|---|---|---|---|
| 1:1 NiMo/C | 297,200 | 0.29 | 4.95 |
| 1:0.5 NiMo/SiO$_2$ | 211,967 | 0.21 | 3.53 |
| 1:0.2 NiRe/C | 183,500 | 0.18 | 3.06 |
| 1:0.25 NiMo/C | 135,833 | 0.13 | 2.26 |
| 1:0.25 NiW/SiO$_2$ | 133,800 | 0.13 | 2.23 |
| 1:0.1 NiMo/C | 82,167 | 0.08 | 1.37 |
| 1:0.1 NiV/SiO$_2$ | 76,833 | 0.08 | 1.28 |
| 1:0.5 NiNb/SiO$_2$ | 40,433 | 0.04 | 0.67 |
| 1:0.5 NiTi/SiO$_2$ | 68,567 | 0.07 | 1.14 |
| Pt/C | 18,700 | 0.06 | |
| Ni/SiO$_2$ | 19,133 | 0.02 | 0.32 |
| Rh/C | 12,700 | 0.02 | 0.07 |
| Co/SiO$_2$ | 740 | 0.001 | |
| FePK/Al$_2$O$_3$ | 361 | 0.00 | |
| 1:0.1 RhMo/C | 192,500 | 0.33 | |

TABLE 5B-continued

2-HY-THP Results: Catalyst Screening (More)

| Catalyst | Rate per gram Metal (µmol/ (min*g metal)) | Rate per Total Parent Metal Sites (1/s) | Rate per Parent Metal Surface Sites (1/s) |
|---|---|---|---|
| 1:1RhRe/C | 192,500 | 0.33 | |
| BASF Cu | 306 | 0.0003 | |

Reaction conditions: T = 120° C., P = 950 psi H$_2$, (64.6 atm), 1 wt% 2-HY-THP/H$_2$O Based on the low conversion results presented in Tables 5A and 5B, additional high conversion reactions were studied for the 2-HY-THP to 1,5-PD hydrogenation reaction. See Table 6.

TABLE 6

Catalyst Screening: High-Conversion Reactions

| Catalyst | Conversion (%) | Selectivity to 1,5-PD (%)* | Selectivity to 1,5-PD based on product area (assumes same sensitivity):* |
|---|---|---|---|
| Cu/Al$_2$O$_3$ | 75.1 | 88.7% | 79.3% |
| Ni/SiO$_2$ | 99.1 | 100.0% | 94.2% |
| Ni/SiO$_2$ | 94.2 | 100.0% | 87.1% |
| Ni/SiO$_2$ | 73.1 | 100.0% | 97.5% |
| 1:0.5 NiMo/SiO$_2$ | 99.8 | 100.0% | 96.4% |
| 1:0.5 NiMo/SiO$_2$ | 85.3 | 100.0% | 97.9% |
| 1:0.5 NiNb/SiO$_2$ | 98.1 | 100.0% | 97.0% |
| 1:0.5 NiTi/SiO$_2$ | 99.3 | 100.0% | 90.5% |
| 1:0.1 NiV/SiO$_2$ | 99.3 | 100.0% | 89.0% |
| 1:0.25 NiW/SiO$_2$ | 99.4 | 100.0% | 94.7% |
| 1:0.15 PtMo/C | 69.2 | 98.0% | 90.8% |
| 1:0.1 RhMo/C | 99.5 | 100.0% | 96.5% |
| 1:0.1 RhMo/C | 97.5 | 100.0% | 97.2% |
| 1:0.1 RhMo/C | 86.2 | 100.0% | 92.8% |
| 1:1 RhRe/C | 99.6 | 100.0% | 98.3% |
| 1:1 RhRe/C | 98.0 | 100.0% | 96.4% |
| 1:1 RhRe/C | 97.2 | 100.0% | 94.3% |

Reaction Conditions: T = 120° C., P = 950 psi H$_2$, 1 wt% 2-HY-THP/H$_2$O
*The sensitivities showed that the selectivity to 1,5-PD was 100%. There was an additional small peak for nickel catalysts which is why the selectivities have also been calculated based on the areas.

TABLE 7

2-HY-THP Hydrogenation Rates over Pt Catalysts

| Catalyst | Pretreatment | 2-HY-THP Conversion Rate (mmol/g/min) | 2-HY-THP Conversion rate (mmol/g-Pt/min) | # of sites (µmol/g) | TOF (1/min) |
|---|---|---|---|---|---|
| 0.59 wt % Pt/H-ZSM5 (impregnation) | ER @ 300° C. & IR @ 200° C. | 1.8 | 314 | 5.54 | 329 |
| 5 wt % Pt/SiO$_2$ (Insoo) | Reduction @ 200° C. | 0.3 | 6.1 | 38 | 8 |
| 0.2 wt % Fe-Pt/SiO$_2$ | Reduction @ 200° C. | 8.5 | 171 | 20.8 | 410 |

Reaction Conditions: T = 120°C., P = 500 psi H$_2$, 10 wt% 2-HY-THP/H$_2$O

Figure 1:
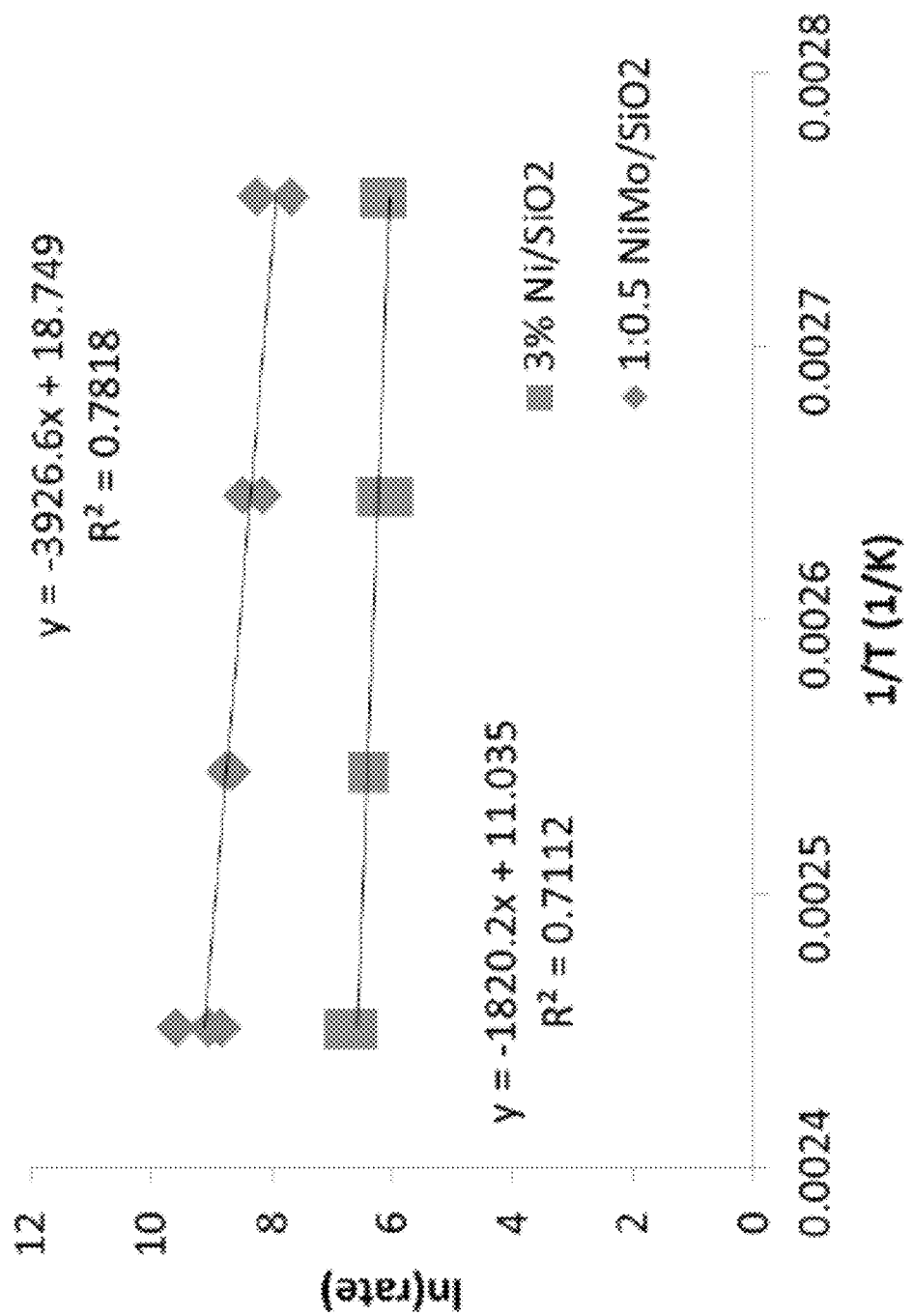
FIG. 1 is a graph depicting the results of activation energy studies for Ni and NiMo catalysts from 90° C. to 135° C. ■=3% Ni/SO$_2$. ◆=1.0:0.5 NiMo/SiO$_2$.

Turning to the figures, FIG. 1 is a graph depicting the results of activation energy studies for Ni and NiMo catalysts from 90° C. to 135° C. ■=3% Ni/SO$_2$. ♦=1.0:0.5 NiMo/SiO$_2$. The activation energy for the hydrogenolysis of 2-HY-THP using a Ni catalyst was calculated to be 15.1+/−9.6 kJ/mol; while the corresponding value when using NiMo was calculated to be 32.6+/−15.4 kJ/mol. While not being limited to any specific underlying phenomenon or mechanism, the substantial difference in the reaction rate when using these two catalysts must be a function of the entropy of formation of the transition state.

Figure 2:
FIG. 2 is a graph depicting catalyst stability. Conversion percent is shown on the Y-axis; time-on-stream (TOS) in hours is shown on the X-axis. ■=Ni/C (200R). ◆=Ni/C (400R). ▲=Ni/SiO$_2$.

FIG. 2 is a graph depicting catalyst stability. Conversion percent is shown on the Y-axis; time-on-stream (TOS) in hours is shown on the X-axis. ■=Ni/C (200R). ♦=Ni/C (400R). ▲=Ni/SiO$_2$. Carbon and silica-supported Ni are not overly stable at a reduction temperature of 200° C. and did not show improved results when a higher reduction temperature of 400° C. was used. Co—TiO$_2$ (20 wt % 2-HY-THP in flow reactor) showed a strong metal-support interaction resulting in 100% yields to 1,5-PD observed.

Figure 3:
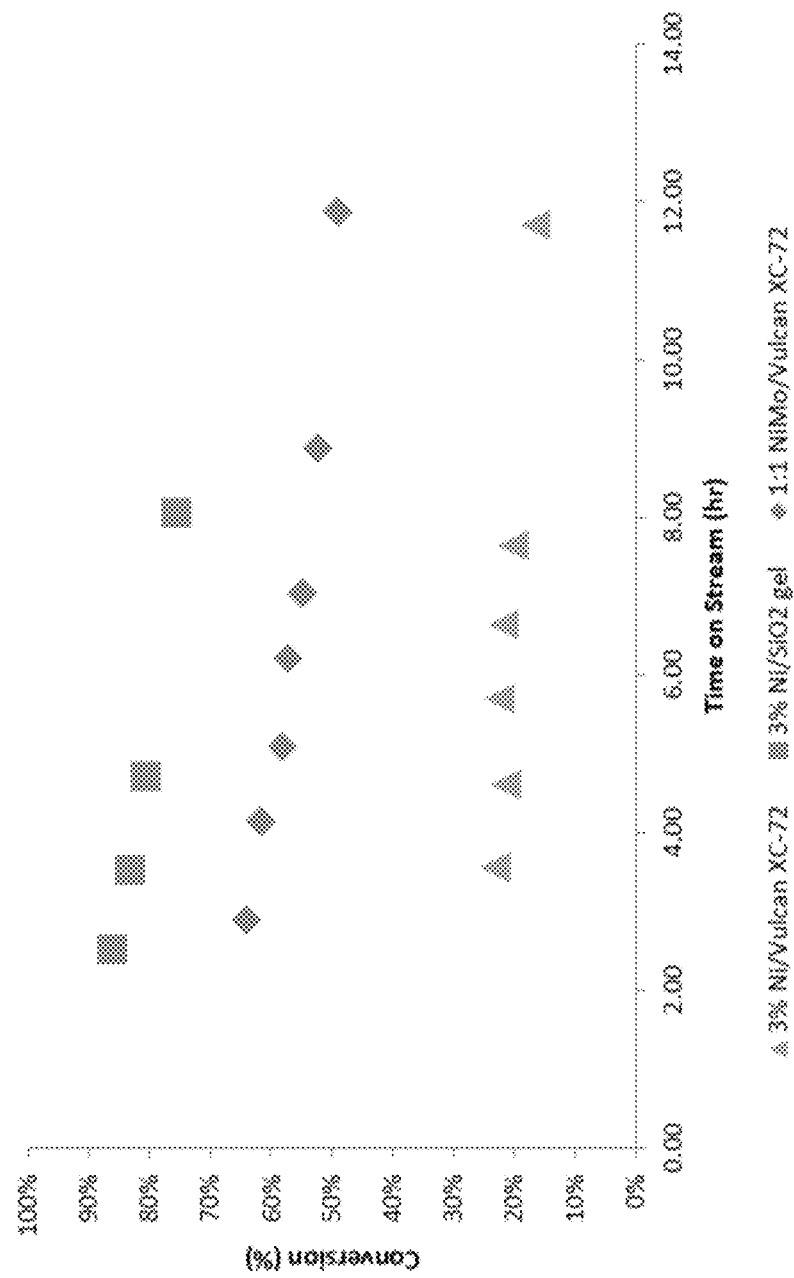
FIG. 3 is a graph depicting catalyst stability. Conversion percent is shown on the Y-axis; time-on-stream (TOS) in hours is shown on the X-axis. ■=3% Ni/SiO$_2$. ◆=1:1 NiMo/Vulcan Carbon (105° C.) ▲=3% Ni/Vulcan Carbon (120° C.).

FIG. 3 is another graph depicting catalyst stability. Conversion percent is shown on the Y-axis; time-on-stream (TOS) in hours is shown on the X-axis. ■=3% Ni/SiO$_2$. ♦=1:1 NiMo/Vulcan Carbon (105° C.) ▲=3% Ni/Vulcan Carbon (120° C.). A reduction temperature of 550° C. improved the stability of Ni/C catalysts. During the reduction step, the temperature was ramped to 550° C. over the course 6 hours and then held steady for 2 hours at 550° C. The rates at the first stable drain (µmol/min/g catalyst) were:
3% Ni/C: 59
3% Ni/SiO$_2$: 230
1:1 NiMo/C: 4250

The reaction conditions for Ni were: T=120° C., P=700 psi H$_2$, 1 wt % 2-HY-THP/H$_2$O, WHSV=1.6 h$^{-1}$. The reaction conditions for NiMo were: T=105° C., P=700 psi H$_2$, 1 wt % 2-HY-THP/H$_2$O, WHSV=40.7 h$^{-1}$.

Figure 4:
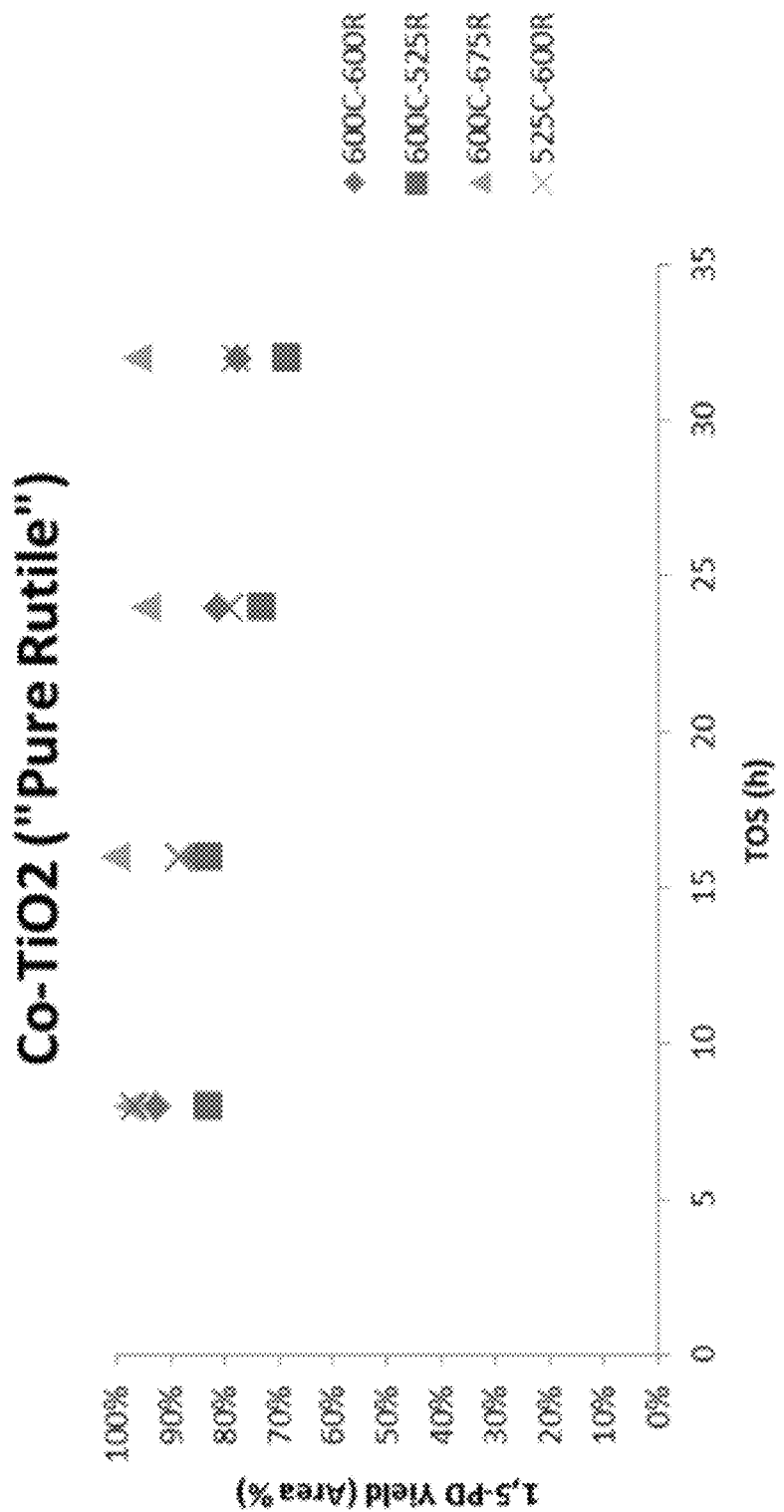
FIG. 4 is a graph depicting catalyst stability of a Co—TiO$_2$ catalyst (TiO$_2$ pre-calcined at 750° C.) at different pretreatment temperatures. 1,5-PD yield percentage is shown on the Y-axis; time-on-stream (TOS) in hours is shown on the X-axis. The pretreatment consisted of a calcination ('C') followed by a reduction ('R') with the temperatures of each given in degrees Celsius. ◆=600C-600R. ■=600C-525C. ▲=600C-675R. X=525C-600R.

FIG. 4 is a graph depicting catalyst stability of a Co—TiO$_2$ catalyst at different pretreatment temperatures. 1,5-PD yield percentage is shown on the Y-axis; time-on-stream (TOS) in hours is shown on the X-axis. The pretreatment consisted of a calcination ('C') followed by a reduction ('R') with the temperatures of each given in degrees Celsius. ♦=600C-600R. ■=600C-525C. ▲=600C-675R. X=525C-600R. The Co—TiO$_2$ was synthesized by impregnation of Co onto pure rutile TiO$_2$ support (calcined before impregnation at 750° C.) up to 5 wt % Co. The reaction conditions for all catalysts were: T=120° C., P=650 psi H$_2$, 1 wt % 2-HY-THP/H$_2$O, WHSV=0.95 h$^{-1}$.

Figure 5:
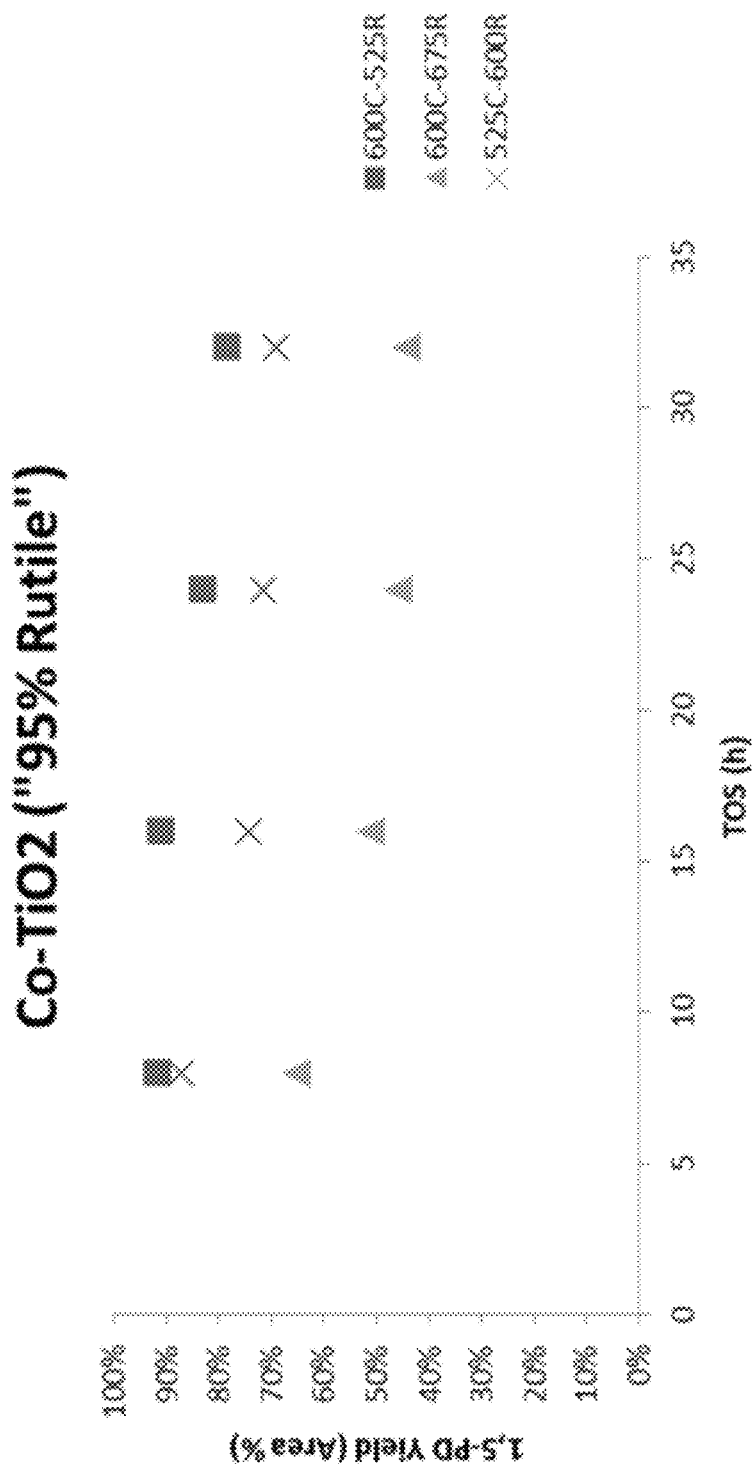
FIG. 5 is a graph depicting catalyst stability of a Co—TiO$_2$ catalyst (TiO$_2$ pre-calcined at 700° C.) at different pretreatment temperatures. 1,5-PD yield percentage is shown on the Y-axis; time-on-stream (TOS) in hours is shown on the X-axis. The pretreatment consisted of a calcination ('C') followed by a reduction ('R') with the temperatures of each given in degrees Celsius. ■=600C-525C. ▲=600C-675R. X=525C-600R.

FIG. 5 is a graph depicting catalyst stability of a Co—TiO$_2$ catalyst at different pretreatment temperatures. 1,5-PD yield percentage is shown on the Y-axis; time-on-stream (TOS) in hours is shown on the X-axis. The pretreatment consisted of a calcination ('C') followed by a reduction ('R') with the temperatures of each given in degrees Celsius. ■=600C-525C. ▲=600C-675R. X=525C-600R. The Co—TiO$_2$ was synthesized by impregnation of Co onto an approximately 95% rutile/5% anatase TiO$_2$ support (calcined before impregnation at 700° C.) up to 5 wt % Co. The reaction conditions for all catalysts were: T=120° C., P=650 psi H$_2$, 1 wt % 2-HY-THP/H$_2$O, WHSV=0.95 h$^{-1}$.

Figure 6:
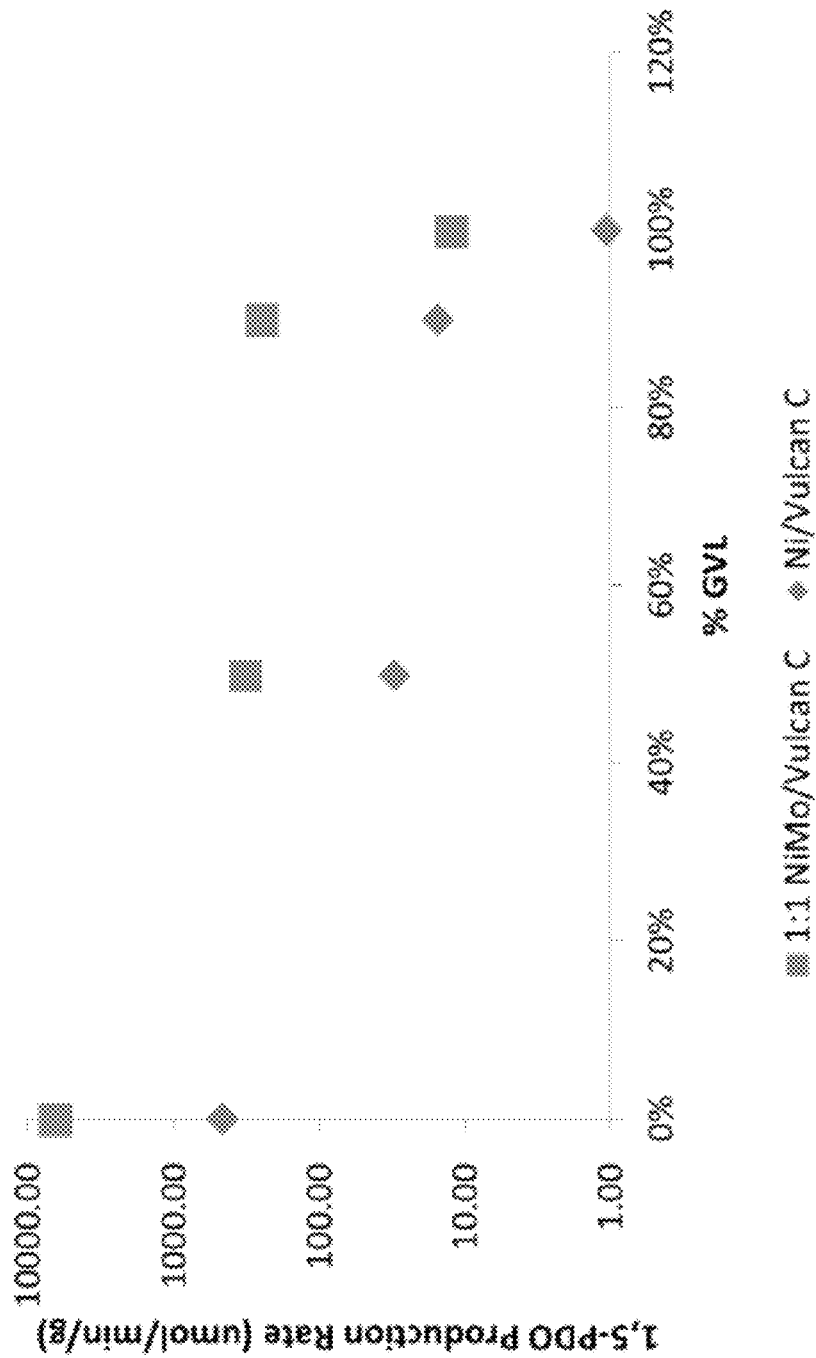
FIG. 6 is a graph depicting the effect of varying the concentration of GVL on hydrogenolysis. ▲=3% Ni/Vulcan Carbon (120° C.). ■=3% Ni/SiO$_2$ (120° C.).

FIG. 6 is a graph depicting the effect of varying the concentration of gamma-valerolactone (GVL) on hydrogenolysis. ▲=3% Ni/Vulcan Carbon (120° C.). ■=3% Ni/SiO$_2$ (120° C.). FIG. 6 shows that reaction rates are drastically reduced in a water and polar aprotic solvent mixture. The reaction conditions were: T=120° C., P=950 psi H$_2$, 1 wt % 2-HY-THP/H$_2$O.

Figure 7:
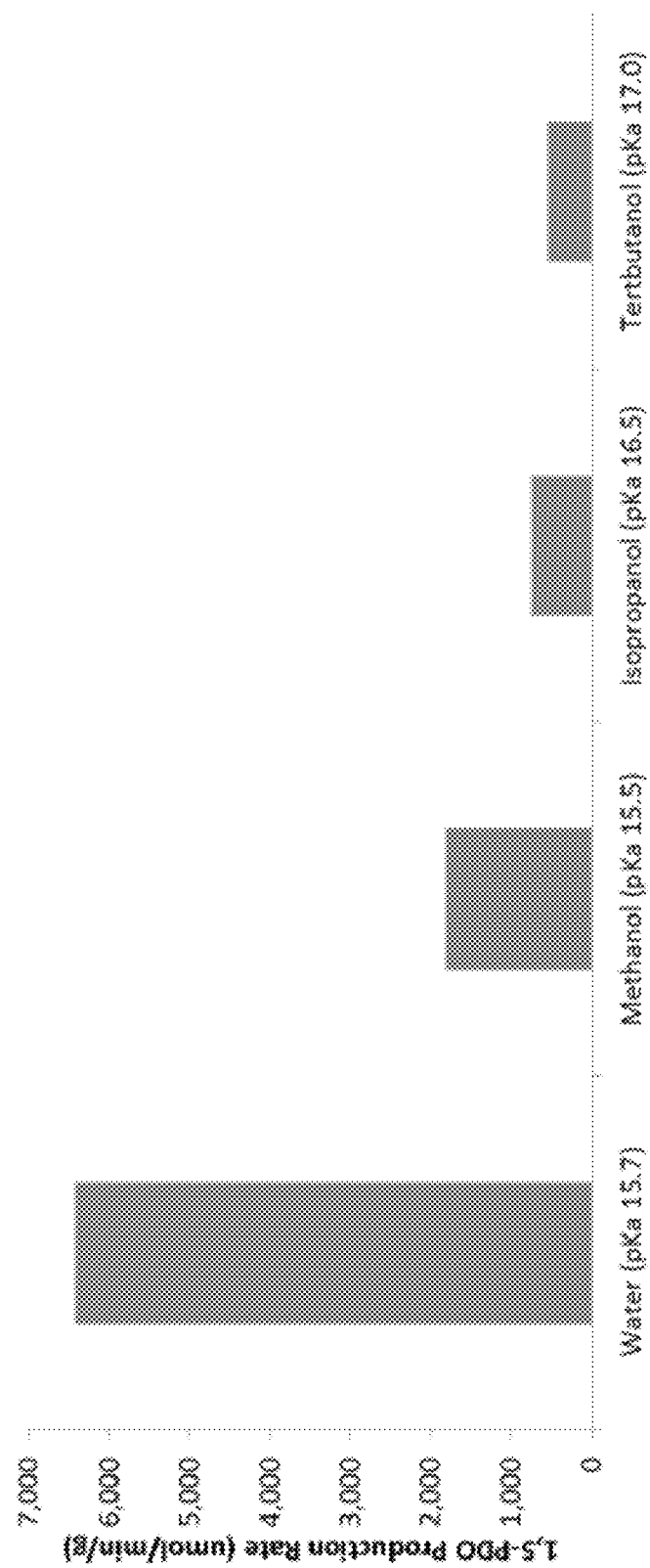
FIG. 7 is a histogram depicting the effect of solvent selection on hydrogenation rates.

FIG. 7 is a histogram depicting the effect of solvent selection on hydrogenolysis rates. As shown in the figure, water works best among the solvents tested, but primary, secondary, and/or tertiary short-chain alcohols may also be used as solvents. The reaction conditions were: T=120° C., P=950 psi H$_2$, 1 wt % 2-HY-THP.

Figure 8:
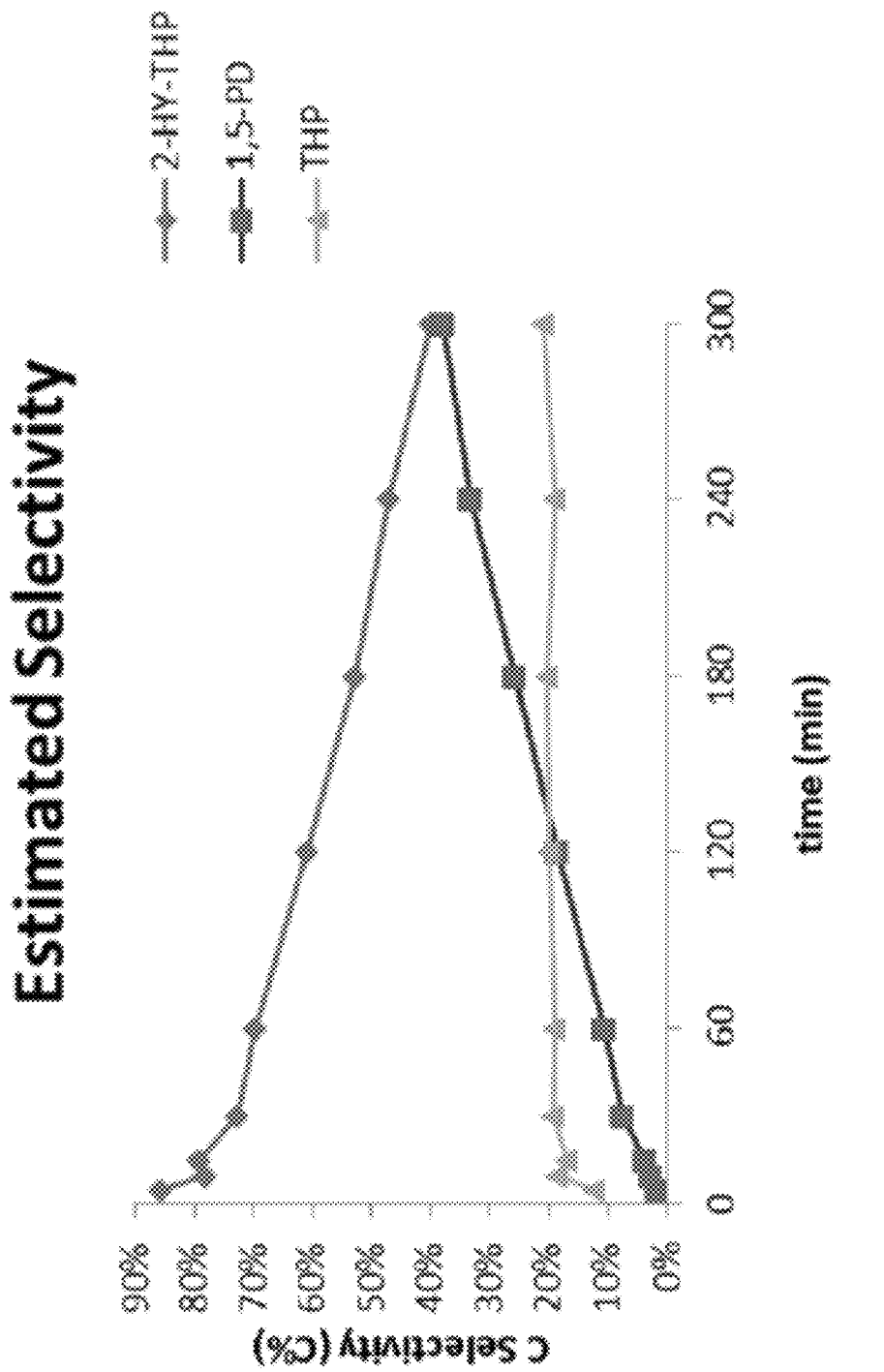
FIG. 8 is a graph depicting product selectivity results for a one-pot hydration-hydrogenation reaction of 20 wt % DHP/H$_2$O over a RhRe/C catalyst at 120° C. for 4 h. ◆=2-HY-THP. ■=1,5-PD. ▲=THP.

FIG. 8 is a graph depicting estimated product selectivity results for a one-pot hydration-hydrogenolysis reaction of 20 wt % DHP/H$_2$O over a RhRe/C catalyst at 120° C. for 4 h. ♦=2-HY-THP. ■=1,5-PD. ▲=THP. The reaction conditions were 20 wt % DHP/H$_2$O over a RhRe/C catalyst at 120° C. for 4 hours in a Parr reactor. Selectivity was based on product selectivity (rather than reactant conversion) because the data for DHP are unreliable due to its limited solubility in water. As shown in the figure, DHP converts to 2-HY-THP and THP at reaction onset, while the production of 1,5-PD is essentially linear over the time course of the experiment.

Figure 9:
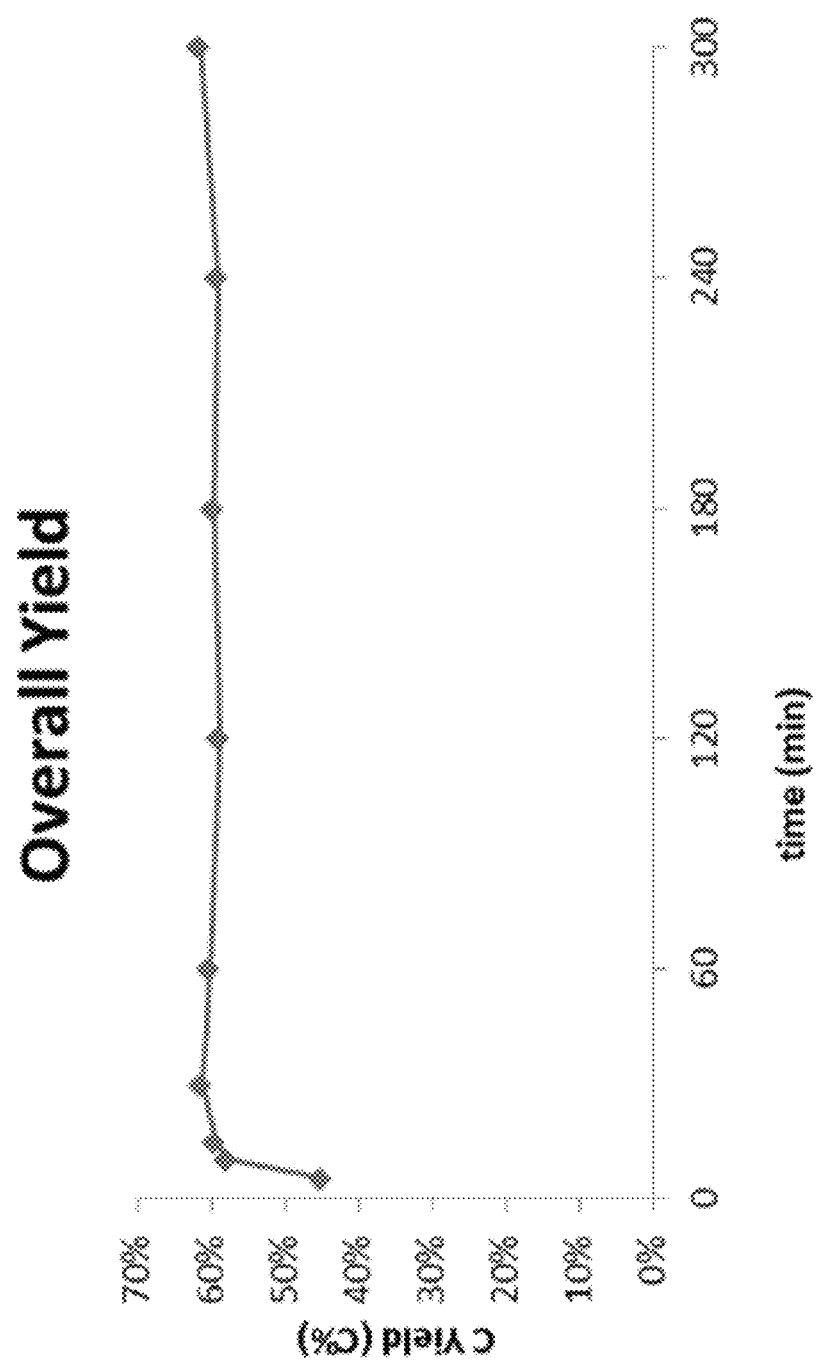
FIG. 9 is a graph depicting overall yield results for a one-pot hydration-hydrogenolysis reaction of 20 wt % DHP/H$_2$O over a RhRe/C catalyst at 120° C. for 4 h.

FIG. 9 is a graph depicting overall yield results for a one-pot hydration-hydrogenolysis reaction of 20 wt % DHP/H$_2$O over a RhRe/C catalyst at 120° C. for 4 h. The absolute yield in this particular experiment, and shown in FIG. 9, is low due to a calibration error in the gas chromatograph used. However, the graph shows that the ultimate yield is reached early in the run (well under 60 min) and remains steady throughout the 300 min reaction.

Figure 10:
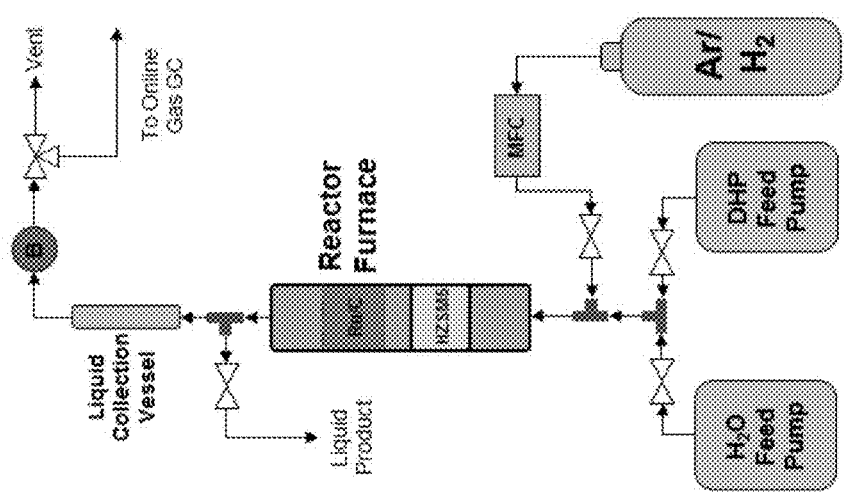
FIG. 10 is a schematic diagram of a dual-pump, continuous-flow reactor employed for DHP hydration flow studies over HZSM5. H$_2$ gas and a second catalyst bed comprising Ru/C was employed for dual-bed hydration/hydrogenation reactions (see Table 9). "MFC"=Mass-flow controller; "B"=back-pressure regulator.

The method disclosed herein can be conducted batchwise, continuously, or semi-continuously. FIG. 10, for example, depicts in schematic form a dual-pump, continuous-flow reactor employed for DHP hydration flow studies using HZSM5 as the solid metal catalyst for the hydration step, coupled with a second catalyst bed containing Ru on a carbon support to catalyst the hydrogenation reaction that yields the 1,5-PD. H$_2$ gas and a second catalyst bed comprising Ru/C was employed for dual-bed hydration/hydrogenation reactions. "MFC"=Mass-flow controller; "B"=back-pressure regulator. The temperature of the reactor furnace is controlled by a conventional thermostat, not shown.

More specifically, a two foot long reactor tube (316 stainless steel, ¼ inch O.D., 0.18 inch I.D.) was filled with the catalyst beds or inert glass beads (Sigma Aldrich, St. Louis, Mo. unwashed, 30-40 US sieve), held at each end by quartz wool. The reactor tube was contained inside a tube furnace equipped with aluminum filler rods for uniform heat distribution (not shown). Both ends of the furnace were sealed with quartz wool. The reactor was pressurized with Ar gas to 500 psi. A back-pressure regulator at the reactor system outlet was set at 500 psi to hold at pressure while allowing gas flow through the system. The reactor furnace controller was set to the desired reaction temperature. Two separate liquid HPLC pumps (Varian ProStar 210 Series) (Agilent, Inc. Santa Clara, Calif.) were used due to the immiscibility of DHP in water. DHP and DI water were flowed separately at a 1:4 mass ratio (20-50 wt % DHP) into a ¼ inch tee junction where they mixed. The DHP:H$_2$O mixture flowed upwards where it was combined with Ar flow at 40 mL/min sccm. Inert Ar was flowed for gas phase analysis; an experiment with no Ar flow confirmed that the gas flow did not have any noticeable effects on the DHP hydration rate. Liquid products accumulated in a stainless-steel gas-liquid separator (300 mL) at the top of the reactor. Liquid samples were collected by first closing the inlet and outlet ball valves of the reactor to isolate the system. The outlet needle valve at the bottom of the liquid collection vessel was opened to collect liquid product into a container for filtration and analysis. Inlet and outlet ball valves were re-opened to continue flow through the reactor.

The initial time-on-stream (TOS=0) is defined as the first steady state data point for activation rate experiments. This was normally taken after 8-14 h of operation. Product carbon yields were calculated on a total mol C basis as shown in Equation 1. The product concentration (mol/L) was measured by gas chromatography. Reaction rates were calculated according to Equation 2. The reactor void volume was measured to be 3.3 cm$^3$ [void fraction(s)=0.40].

$$\text{Yield } (C \%) = \frac{\text{mol } C \text{ product}}{\text{mol } C \text{ DHP fed}} = \qquad (3)$$

$$\frac{\left(\frac{\text{mol product}}{L}\right)_A \cdot \text{Volume}_A(L) \cdot \left(\frac{\text{mol } C \text{ product}}{\text{mol product}}\right)}{DHP \text{ flowrate}\left(\frac{\text{mol } C}{\text{min}}\right) \cdot \text{Total sample time (min)}}$$

$$\text{Reaction Rate}\left(\frac{\mu\text{mol}}{\text{min} \cdot L}\right) = \qquad (4)$$

$$\frac{\left(\frac{\text{mol}_2 HYTHP \text{ product}}{L}\right)_A \cdot \text{Volume}_A(L) \cdot \left(\frac{1E_6 \mu\text{mol}}{\text{mol}}\right)}{\text{Total sample time (min)} \cdot \text{Void Volume }(L)}$$

Gas Chromatography (GC): Reaction product solutions were placed in a separation funnel for 10 minutes. The volumes of the organic and aqueous phases were recorded by funneling each phase into a graduated cylinder. The aqueous and organic products were filtered with 0.22 μm polyethersulfone and polytetrafluoroethelyne filter membranes, respectively, before analysis. Liquid products were injected into a Shimadzu Gas Chromatograph with a Flame Ionization Detector (FID). The injection port and FID temperature was 240° C. The injection volume was 1 μL and a split ratio of 100 was used. The GC column was a Restek RTX-VMS capillary column (length: 30 m, ID: 0.25 mm, film thickness: 1.4 μm). The column temperature was held at 40° C. for 1 min, ramped at 20° C./min to 240° C., and held at 240° C. for 13 min.

Gas Chromatography-Mass Spectrometry (GC-MS): Mass spectrometry of product solutions was performed on a two-dimensional (2D) gas chromatography-mass spectroscopy (GC×GC-MS) with both a FID (Agilent, 7890B) and a mass selective detector (MSD; Agilent, 5977A). A flow modulator (CFP; Agilent, G3487A) was installed to make a GC×GC system. Two capillary columns, DB-17 (Agilent, Catalog No. 121-1723) and CP-Sil 5 CB (Agilent, Catalog No. CP7700), were set up in series with the CFP for 2D separation. H2 carrier gas was flowed at 0.7 mL/min and 25 mL/min through the first and second dimension columns, respectively. In all experiments, both the first and second dimensions were operated in constant flow mode. Ion fragment patterns were compared to known patterns in the NIST mass spectrometry database for product identification.

NMR: Products were analyzed by proton and $^{13}$C NMR. A Bruker standard pulse sequence "zgig30" was used for the quantitative $^{13}$C experiments with the following parameters: an inter-scan relaxation delay of 12 s, a sweep width of 240 ppm centered at 110 ppm, acquiring 59,520 data points with an acquisition time of 1 s, and 128 scans. (Bruker Corp., Billerica, Mass.) The $^{13}$C Dept-135 experiments used the Bruker standard pulse sequence "deptsp135" with the following parameters: an inter-scan relaxation delay of 2 s, a sweep width of 240 ppm centered at 110 ppm, acquiring 59,520 data points with an acquisition time of 1 s, and 128 scans. Mestrelab Research's MestReNova software was used to process the spectra and the spectra were referenced to a TMS internal standard at 0 ppm. (Mestrelab Research L.C., Santiago de Compostela, Spain.)

2D NMR (HSQC and HMBC) experiments were carried out on a Bruker Biospin (Billerica, Mass.) AVANCE III HD 600 MHz spectrometer fitted with a TCI-F cryoprobe. Bruker standard pulse sequence "hsqcedetgpsisp2p3" was used for the HSQC experiment with the following parameters: 14 ppm sweep width in F2 ($^1$H), centered at 4.7 ppm, acquiring 3,366 data points, 240 ppm sweep width centered at 110 ppm in F1 ($^{13}$C) acquiring 1,309 increments, 4 scans per increment, and a 2.0 s relaxation delay. Bruker standard pulse sequence "hmbcgplpndprqf" was used for the HMBC experiment with the following parameters: 14 ppm sweep width centered at 4.7 ppm in F2 ($^1$H) acquiring 3366 data points, 240 ppm sweep width centered at 110 ppm in F1

($^{13}$C) acquiring 1309 increments, 4 scans per increment, and a 2.0 s relaxation delay. Bruker's Topspin 3.5 software was used to process spectra.

Figure 11:
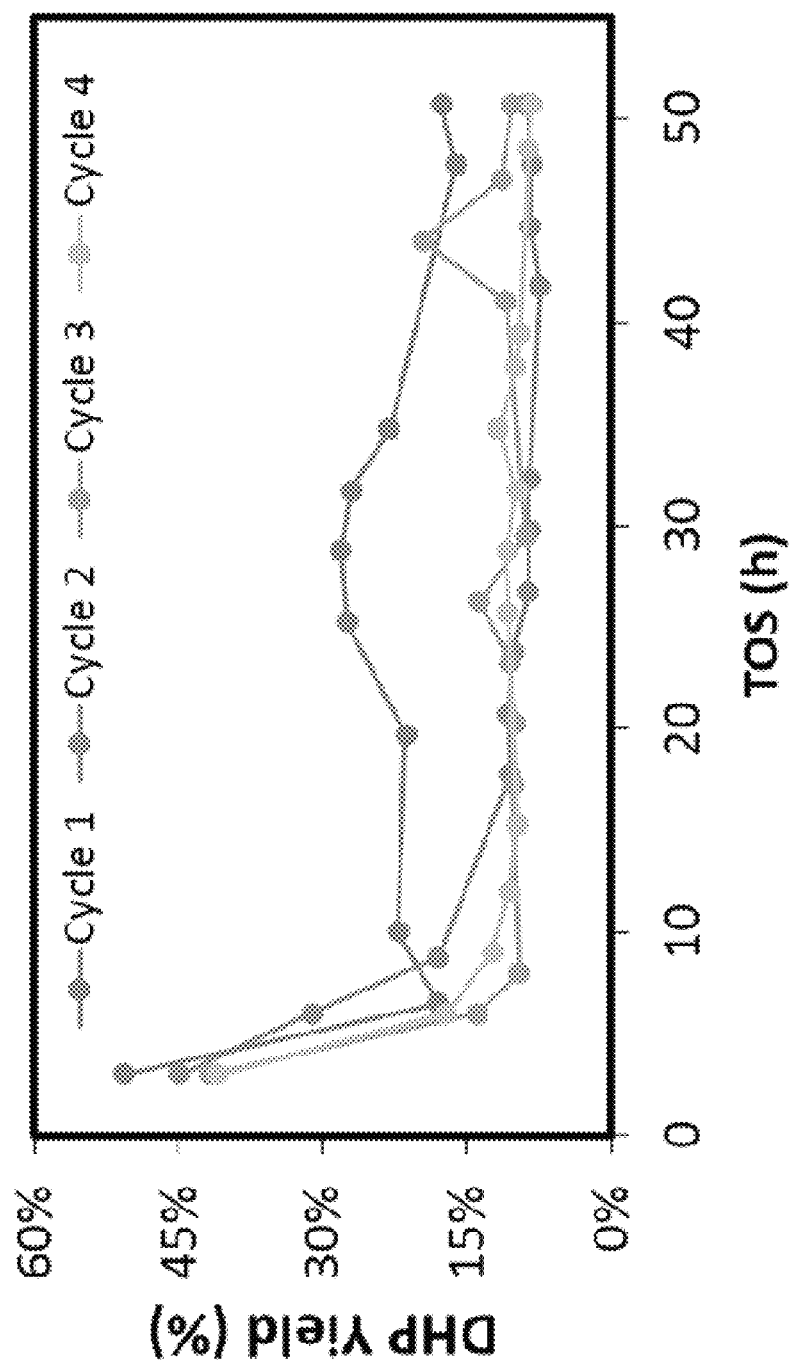
FIG. 11 is a graph depicting the yield of dihydropyran (DHP) from the dehydration of tetrahydrofufural alcohol (THFA) over γ-Al$_2$O$_3$ in the vapor phase. Four cycles are shown with the catalyst regenerated with a 500° C. calcination step between each cycle. 93% DHP Yields achieved at high conversion.

The DHP used as the feed in FIG. 10 is preferably derived from biomass via the dehydration of THFA. As shown in FIG. 11, this was accomplished very efficiently by dehydrating tetrahydrofurfuryl alcohol (THFA) over γ-Al$_2$O$_3$ in the vapor phase to yield DHP. (Other transition metal oxides also may be used, e.g. silica, titania, vanadia, ceria, tin oxide, niobia, zirconia, etc.) The THFA is derivable from raw biomass. As shown in FIG. 11, very high conversions of THFA and concomitant yields of dihydropyran (DHP) were achieved using this approach. Additionally, the γ-Al$_2$O$_3$ catalyst was easily regenerated by calcining it at 500° C. Calcining the catalyst recovers surface area lost to coking of the catalyst. 93% DHP yields were achieved using this approach.

Figure 12:
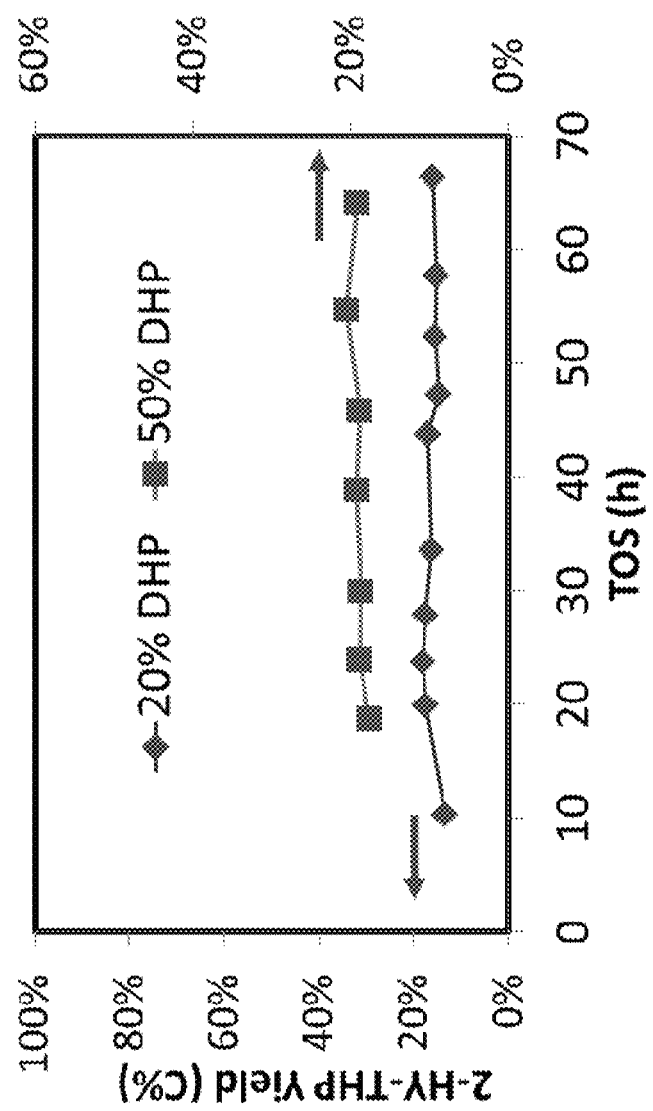
FIG. 12 is a graph depicting 2-HY-THP yield versus time-on-stream ("TOS") for a continuous-flow DHP hydration over HZSM5. Feed: 20 wt % and 50 wt % DHP/H$_2$O, Total Feed WHSV: 260.3 h$^{-1}$ (at 20 wt % feed) and 28.8 h$^{-1}$ (at 50 wt % feed). T=50° C. P=500 psi. Ar flow=40 mL/min.

FIG. 12 is a graph depicting 2-HY-THP yield versus time-on-stream ("TOS") for a continuous-flow DHP hydration to 2-HY-THP over HZSM5 using the reactor shown in FIG. 10. Here, two separate runs were conducted: the first used a feed that was 20 wt % DHP in water; the second used a feed that was 50 wt % DHP in water. The total feed WHSV was 260.3 h$^{-1}$ for the 20 wt % feed and 28.8 h$^{-1}$ for the 50 wt % feed). For both reactions: T=50° C. P=500 psi. Ar flow=40 mL/min. As shown in FIG. 12, yields were higher for the 50 wt % feed (squares) as compared to the 20 wt % feed (diamonds). Both yields, however, were quite acceptable.

To establish a baseline reaction rate of thermal conversion, DHP was hydrated to 2-HY-THP using water at various temperatures in batch reactors, but no catalysts of any sort. Due to its limited solubility in water (<1 wt %), DHP forms an insoluble layer on top of water. The products (primarily 2-HY-THP) formed in the reaction enter the aqueous phase until there is a single aqueous phase at total DHP conversion. The results are tabulated in Table 8.

TABLE 8

DHP Hydration: Temperature Effects (DHP hydrated without catalyst at increasing temperatures)

| Temperature (° C.) | 60 | 60 | 100 | 140 | 180 | 200 |
|---|---|---|---|---|---|---|
| Reaction Time (h) | 2 | 12 | 2 | 2 | 2 | 2 |
| 2-HY-THP | 21.1% | 90.6% | 92.2% | 84.3% | 59.5% | 14.8% |
| 2-2'-HY-THP | 0.3% | 2.5% | 2.3% | 1.1% | 0.6% | 0.1% |
| THP-oxypentanal | 0.4% | 5.2% | 3.8% | 5.2% | 1.9% | 0.3% |
| Total 1,5-PD Precursors | 21.8% | 98.3% | 98.3% | 90.6% | 62.0% | 15.1% |

TABLE 8-continued

DHP Hydration: Temperature Effects (DHP hydrated without catalyst at increasing temperatures)

| Temperature (° C.) | 60 | 60 | 100 | 140 | 180 | 200 |
|---|---|---|---|---|---|---|
| Reaction Time (h) | 2 | 12 | 2 | 2 | 2 | 2 |
| High T Dimer | 0.0% | 0.0% | 0.0% | 1.8% | 7.0% | 1.8% |
| Unidentified GC Products | 2.6% | 1.7% | 1.6% | 2.0% | 1.8% | 2.2% |
| Missing Carbon | — | 0.0% | 0.1% | 5.7% | 29.2% | 80.8% |

Key:
2-HY-THP, 2,2'-HYP-THP, THP-oxypentanal

Figure 13:
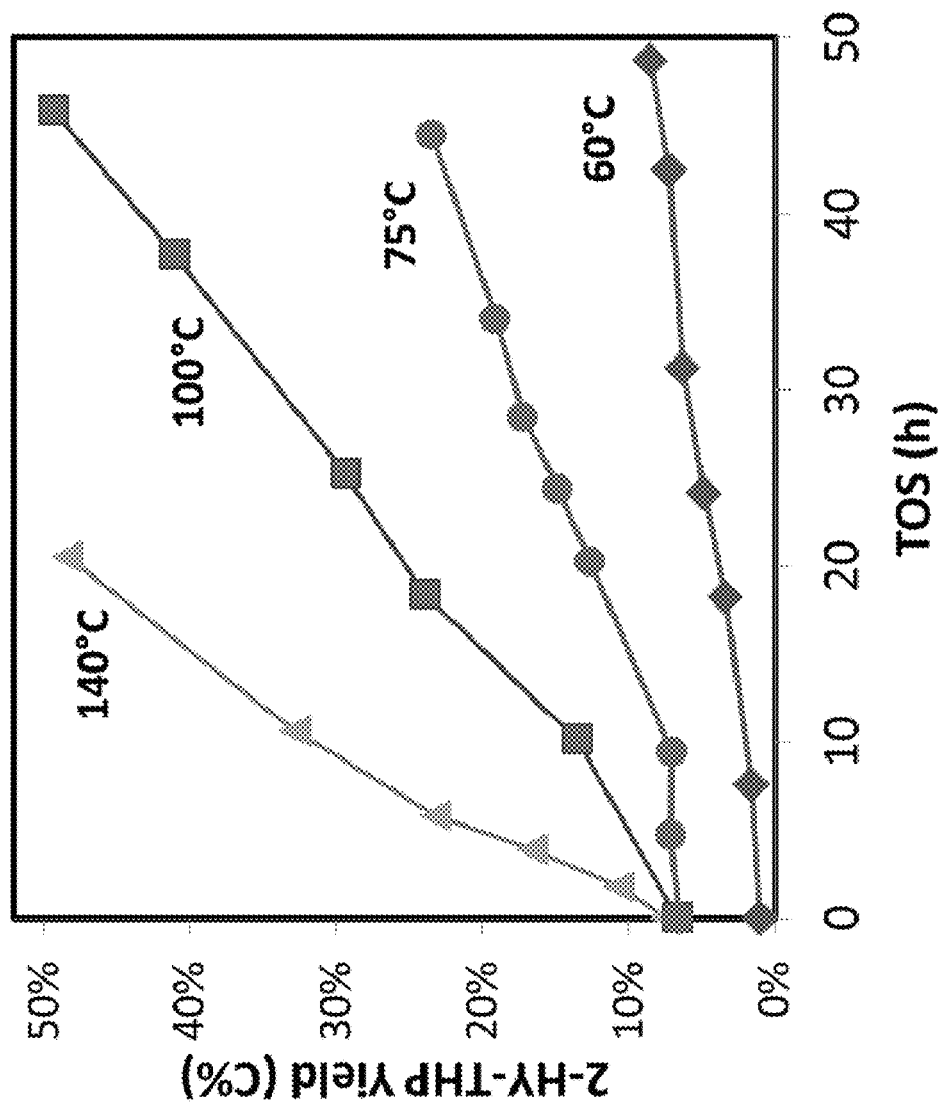
FIG. 13 is a graph depicting the yield of 2-hydroxy-tetrahydropyaran (2-HY-THP) from the hydration of dihydropyran (DHP) without catalyst as a function of time-on-stream at various temperatures (60° C., 75° C., 100° C., and 140° C.). The reaction was conducted in a flow reactor.

All reactions (batch and continuous) gave a final pH of about 3.4. This indicated the presence of carboxylic acids. Active acidic coke forms at the high temperatures, along with a concomitant increase in hydration rates. As can be seen from Table 8, the reactions run at 60° C. and 100° C. both yielded 98.3 wt % 1,5-PD precursors. A graph depicting the corresponding yields of 2-HY-THP at each temperature is shown in FIG. 13. The data shown in FIG. 13 were generated by reactions conducted continuously in the reactor shown in FIG. 10, in the absence of any catalysts. The reactions were run at 60° C. (diamonds), 75° C. (circles), 100° C. (squares), and 140° C. (triangles). Corresponding batch reactions yielded corresponding results (data not shown). Analysis of the reactor contents showed that acidic coke formed at the higher temperatures. The rate of the hydration reaction increased also increased with temperature; note the sharply increasing slopes of the curves shown in FIG. 13 as the temperature increases from 60° C. to 140° C. This gave rise to a hypothesis that the increased rate might be due to the formation of the acidic coke species. Thus, the hydration reaction was then run in the presence of a series of solid acid catalysts. See Table 9. These experiments revealed that a solid acid catalyst greatly increases the rate of the hydrolysis reaction. As can be seen from Table 9, all of the solid acid catalysts used resulted in a much-improved yield of 2-HY-THP from DHP.

TABLE 9

Comparison of 2-HY-THP production rate and Brønsted acid site TOF for the hydration of 0.5 wt % DHP in DI water over various solid acid catalysts in a batch reactor (T: 50° C., P: 500 psi Ar, Reaction time: 1 h)

| Catalyst | Catalyst mass (mg) | 2-HY-THP Yield (C %) | 2-HY-THP Production Rate (μmol/gcat-min) | Brønsted Site Fraction | Brønsted Site Density (mmol/g) | TOF (s$^{-1}$) |
|---|---|---|---|---|---|---|
| No catalyst | — | 0 | 0 | — | — | — |
| γ-Al$_2$O$_3$ | 500 | 3.8 | 4 | 0.40$^a$ | 0.17 | 0.0004 |
| SiO$_2$-Al$_2$O$_3$ | 300 | 7.8 | 13 | 0.79$^a$ | 0.72 | 0.0003 |

TABLE 9-continued

Comparison of 2-HY-THP production rate and Brønsted acid site TOF for the hydration of 0.5 wt % DHP in DI water over various solid acid catalysts in a batch reactor (T: 50° C., P: 500 psi Ar, Reaction time: 1 h)

| Catalyst | Catalyst mass (mg) | 2-HY-THP Yield (C %) | 2-HY-THP Production Rate (μmol/gcat-min) | Brønsted Site Fraction | Brønsted Site Density (mmol/g) | TOF ($s^{-1}$) |
|---|---|---|---|---|---|---|
| CsPTA | 20 | 28.0 | 722 | — | 0.15 | 0.08 |
| ZrP | 5 | 21.1 | 2170 | $0.38^b$ | 1.05 | 0.034 |
| Nafion SAC-13 | 2 | 10.6 | 2727 | $\infty^a$ | 0.14 | 0.325 |
| HZSM5 | 4 | 21.9 | 2822 | $0.51^c$ | 0.41 | 0.223 |
| H-Beta | 2 | 20.1 | 5178 | — | 2.5 | 0.035 |
| Amberlyst-15 | 0.5 | 22.0 | 22662 | $\infty^a$ | 2.86 | 0.132 |
| Amberlyst-70 | 0.5 | 25.3 | 26017 | $\infty^a$ | 2.86* | 0.152 |

$^a$Ronen et. al (2011)
$^b$Ronen et. al. (2013)
$^c$Yu-Ting et. al. (2012)
*Amberlyst-70 acid site density Additionally, experiments were performed showing that the hydration and hydrogenation reactions (starting from DHP) can be performed simultaneously in either a twin-bed continuous reactor such as the one shown in FIG. 10 or batchwise. For exemplary reactions, see Table 10.

TABLE 10

Product yields for the combined hydration-hydrogenation of DHP in a single reactor ((batch or continuous) over Ru/C and solid-acid catalysts.

| Reactor | DHP Loading (wt %) | T (° C.) | H Catalyst | H Catalyst Mass (mg) | Hyd. Catalyst | Hyd. Catalyst Mass (mg) | 2-HY-THP Yield (C %) | THP Yield (C %) | 1,5-PD Yield (C %) | Total Yield (C %) |
|---|---|---|---|---|---|---|---|---|---|---|
| Batch$^a$ | 0.5 | 100 | None | — | A-15$^d$ | 75 | 102.7 | 0.0 | 0.0 | 102.7 |
| Batch$^b$ | 0.5 | 100 | Ru/C | 75 | None | — | 0.0 | 39.8 | 57.7 | 97.5 |
| Batch$^b$ | 0.5 | 100 | Ru/C | 75 | A-15$^d$ | 75 | 0.0 | 11.2 | 77.5 | 88.7 |
| Batch$^b$ | 0.5 | 100 | Ru/C | 50 | None | — | 0.0 | 61.6 | 43.4 | 105.0 |
| Batch$^b$ | 0.5 | 100 | Ru/C | 50 | H-Beta | 750 | 0.0 | 4.7 | 52.1 | 56.8 |
| Continuous$^c$ | 20 | 70 | Ru/C | 750 | HZSM5 | 150 | 0.0 | 0.8 | 100.0 | 100.8 |

*All reactions carried out at 500 psi H$_2$ and resulted in quantitative DHP conversion
$^a$Reaction time: 1.5 h.
$^b$Reaction time: 2 h.
$^c$Catalysts packed in-line in separate catalyst beds (FIG. 10); Feed Flowrate: 0.0344 mL/min; H$_2$ Flowrate: 40 mL/min.
$^d$Amberlyst-15

Figure 14:
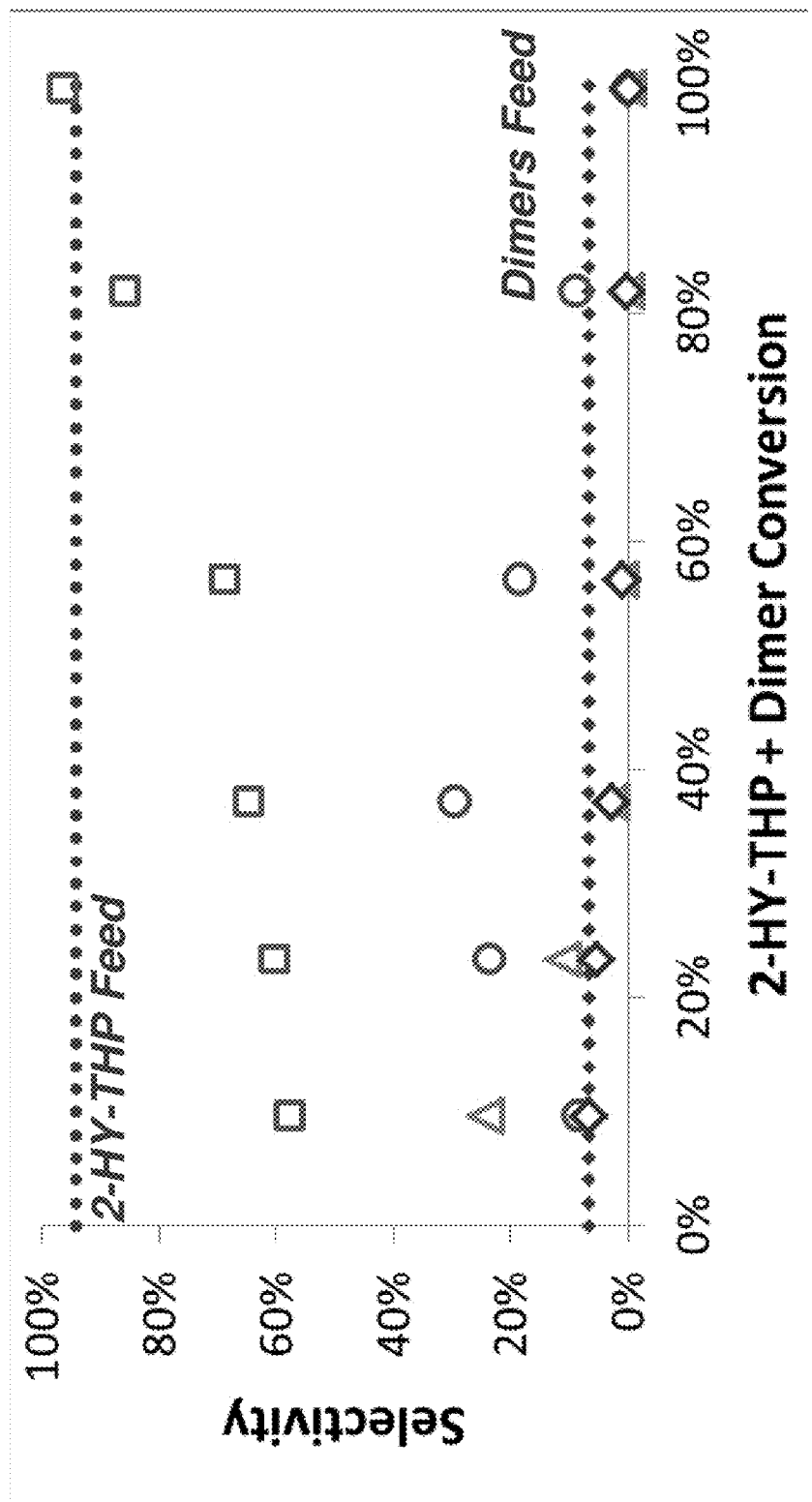
FIG. 14 is a graph depicting hydrogenation of 2-HY-THP to 1,5-pentanediol. The reaction was conducted continuously in a flow reactor over 1% Ru/TiO$_2$ at varying WHSV.

In short, the product mix resulting from the hydration of DHP can be subjected to the final hydrogenation step without any isolation of the intermediate products. The hydrogenation step is preferably carried out in the presence of a metal-containing catalyst, as mentioned previously. The product mix of an exemplary hydrogenation reaction (using the DHP hydration reaction products as the reactant from the hydrogenation reaction) is shown in FIG. 14. The reaction was conducted continuously in the flow reactor shown in FIG. 10 over 1% Ru/TiO$_2$ at varying WHSV. The product mix included 1,5-PD (squares), THP-oxypentanol (circles), THP-oxypentanal (triangles), and 2,2'-HY-TYP (diamonds). However, as shown in FIG. 14, the selectivity to 1,5-PD dominated the reaction. At complete conversion, greater than 97% yield of 1,5-PD was achieved.

The long-term stability of the 2-HY-THP conversion step was tested over a HZSM5-supported Pt catalyst with a 0.59 wt % Pt loading. From FIG. 15 it can be seen that over the conversion of 2-HY-THP to 1,5-PD increases for up to 170 h time-on-stream (TOS). This enhancement of the reaction rate of Pt/HZSM5 over time while using concentrated (10 wt %) feed solutions of 2-HY-THP is promising for the catalyst stability of the hydrogenation step.

In testing HZSM5 as a solid acid catalyst, a host of unsaturated compounds were tested to see which compounds would yield 2-HY-THP (which could then be hydrogenated to yield 1,5-PD). These reactions were run in a batch reactor. The results are presented in Table 11. As shown in the table, both DHP (i.e., 3,4-DHP) and dihydroxyfuran (2,3-DHF) yielded the corresponding 2-hydroxy product (2-hydroxy-tetrahydopyran in the case of DHP and 2-hydroxy-tetrahydofuran in the case of DHF). Analogous results were achieved for 3,6-DHP (which yielded 4-HY-THP) and 2,5-DHF (which yielded 3-HY-THF). These results show that with reactant mix comprising DHP, the HZSM5 catalyst is very effective for hydrating the DHP to the desired intermediate, 2-HY-THP.

Batch reactor experiments were performed in 45 mL or 75 mL Parr Hastelloy autoclaves. After adding a magnetic stir bar, DHP was added to DI water up to 20 wt % in all experiments. All experiments in which kinetic data were obtained were carried out in the 75 mL Parr reactor with 30 g of feedstock (6 g DHP/24 g DI water) due to better mixing conditions. Liquid feed volume and reactor geometry are important considerations for the proper mixing of the organic and aqueous phases in batch mode. Stir rate did not affect hydration rates at these conditions. A stir speed of 750 rpm was used for all experiments. The reactor was purged with Ar two times before pressurizing the reactor to 500 psi. Reactors were heated to the reaction temperature at 4° C./min. After holding for the desired reaction time, reactors were quenched in an ice water bath. Results are presented in Table 11.

TABLE 11

Batch reaction data for the hydration of unsaturated compounds in DI water over HZSM5 at 50° C.

| Feed | Product | Mass HZSM5 (mg) | Reaction Time (h) | Product Yield (C %) | Production rate (µmol/gcat-min) |
|---|---|---|---|---|---|
| 3,4-DHP | 2-HY-THP | 1 | 1 | 7.0% | 2,097 |
| 2,3-DHF | 2-HY-THF | 3 | 1 | 11.5% | 1,147 |
| 3-methyl-2-pentene | 3-methyl-3-pentanol | 2000 | 16 | 6.9% | 0.064 |
| 2-methyl-1-pentene | 2-methyl-2-pentanol | 2000 | 17 | 2.8% | 0.025 |
| Cyclohexene | Cyclohexanol | 2000 | 16 | 1.9% | 0.017 |
| Cyclopentene | Cyclopentanol | 2000 | 18 | 0.2% | 0.0020 |
| 3-methyl-1-pentene | 3-methyl-2-pentanol | 2000 | 40 | 0.5% | 0.0018 |
| 1-penten-3-ol | 2,3-pentanediol | 3000 | 36 | 0.0% | — |
| 3,6-DHP | 4-HY-THP | 4000 | 30 | 0.0% | — |
| 2,5-DHF | 3-HY-THF | 4000 | 25 | 0.0% | — |

*Initial Feed Concentration: 0.06M

What is claimed is:

1. A method of making 1,5-pentanediol, the method comprising:
   (a) dehydrating tetrahydrofurfural alcohol (THFA) to dihydropyran (DHP);
   (b) hydrating at least a portion of the DHP to yield a product mix containing 2-hydroxy-tetrahydropyran (2-HY-THP) and 5-hydroxyvaleraldehyde in the presence of a solid acid catalyst; and
   (c) hydrogenating at least a portion of the product mix of step (b) to 1,5-pentanediol.

2. The method of claim 1, wherein the solid acid catalyst of step (b) is selected from the group consisting of solid Brønsted acid catalysts, solid Lewis acid catalysts, and combinations thereof.

3. The method of claim 1, wherein the solid acid catalyst of step (b) is selected from the group consisting of zeolites, alumina, sulfonic acid-modified polymers, salts of phosphotungstic acid, and zirconium phosphate.

4. The method of claim 1, wherein the solid acid catalyst of step (b) comprises an aluminosilicate zeolite.

5. The method of claim 1, wherein the solid acid catalyst of step (b) comprises HZSM5 or H-Beta.

6. The method of claim 1, wherein step (a) comprises hydrating the THFA by contacting it with a solid acid catalyst.

7. The method of claim 1, wherein step (a) occurs on neat THFA or on an aqueous solution of THFA and the THFA is present in the aqueous solution in a concentration of from about 5 wt % to about 99 wt %.

8. The method of claim 7, wherein step (a) occurs at a temperature of from about 200° C. to about 500° C. and a pressure of from about 1 atm to about 5 atm.

9. The method of claim 8, wherein step (a) occurs at a temperature of from about 275° C. to about 450° C.

10. The method of claim 1, wherein step (b) occurs in the presence of water and at a temperature of from about 20° C. to about 200° C.

11. The method of claim 10, wherein the DHP is present with the water in a concentration of from about 5 wt % to about 80 wt %.

12. The method of claim 11, wherein step (b) occurs at a temperature of from about 20° C. to about 150° C.

13. The method of claim 1, wherein in step (c), at least a portion of the product mix of step (b) is hydrogenated to 1,5-pentanediol by contacting the 2-HY-THP with a catalyst comprising a metal selected from the group consisting of Ti, V, Fe, Co, Cu, Ni, Mo, Rh, Ru, Pd, Au, Ag, Ir, Re, Pt, and combinations thereof.

14. The method of claim 13, wherein in step (c), at least a portion of the product mix of step (b) is hydrogenated to 1,5-pentanediol by contacting the 2-HY-THP with a catalyst selected from the group consisting of Ru, NiMo, NiRe, NiV, NiTi, Ni, Fe, Co, Rh, RhRe, RhMo, Pt and PtMo.

15. The method of claim 13, wherein the catalyst is deposited on a support.

16. The method of claim 15, wherein the support is selected from the group consisting of carbon and metal oxides.

17. A method of making 1,5-pentanediol, the method comprising:
   (a) dehydrating tetrahydrofurfural alcohol (THFA) to dihydropyran (DHP) by contacting the THFA with a solid acid catalyst at a temperature of from about 200° C. to about 500° C., and a pressure of from about 1 atm to about 5 atm;
   (b) hydrating at least a portion of the DHP to yield a product mix containing 2-hydroxy-tetrahydropyran (2-HY-THP) and 5-hydroxyvaleraldehyde in the presence of a solid acid catalyst at a temperature of from about 20° C. to about 200° C.; and
   (c) hydrogenating at least a portion of the product mix of step (b) to 1,5-pentanediol by contacting the 2-HY-THP with a catalyst comprising a metal selected from the group consisting of Ti, V, Fe, Co, Cu, Ni, Mo, Rh, Ru, Pd, Au, Ag, Ir, Re, Pt, and combinations thereof.

18. The method of claim 17, wherein in step (c), at least a portion of the product mix of step (b) is hydrogenated to 1,5-pentanediol by contacting the 2-HY-THP with a catalyst selected from the group consisting of Ru, NiMo, NiRe, NiV, NiTi, Ni, Fe, Co, Rh, RhRe, RhMo, Pt and PtMo.

19. The method of claim 17, wherein the catalyst of step (c) is deposited on a support.

20. The method of claim 19, wherein the support is selected from the group consisting of carbon oxides, metal oxides, and zeolites.

21. The method of claim 17, wherein all of steps (a), (b), and (c) are performed in the absence of a noble metal.

22. The method of claim 17, wherein the solid acid catalyst of step (b) is selected from the group consisting of solid Brønsted acid catalysts, solid Lewis acid catalysts, and combinations thereof.

23. The method of claim 17, wherein the solid acid catalyst of step (b) is selected from the group consisting of zeolites, alumina, sulfonic acid-modified polymers, salts of phosphotungstic acid, and zirconium phosphate.

24. The method of claim 17, wherein the solid acid catalyst of step (b) comprises an aluminosilicate zeolite.

25. The method of claim 17, wherein the solid acid catalyst of step (b) comprises HZSM5 or H-Beta.

* * * * *